United States Patent
Clark-Lewis et al.

(10) Patent No.: US 6,946,445 B1
(45) Date of Patent: Sep. 20, 2005

(54) THERAPEUTIC CHEMOKINE RECEPTOR ANTAGONISTS

(75) Inventors: Ian Clark-Lewis, Vancouver (CA); Jiang-Hong Gong, Vancouver (CA); Vincent Duronio, Delta (CA)

(73) Assignee: The University of British Columbia, Vancouver (CA)

(*) Notice: Subject to any disclaimer, the term of this patent is extended or adjusted under 35 U.S.C. 154(b) by 0 days.

(21) Appl. No.: 09/646,192
(22) PCT Filed: Mar. 12, 1999
(86) PCT No.: PCT/CA99/00221
§ 371 (c)(1), (2), (4) Date: Mar. 2, 2001
(87) PCT Pub. No.: WO99/47158
PCT Pub. Date: Sep. 23, 1999

(30) Foreign Application Priority Data

Mar. 13, 1998 (CA) .............................................. 2226391
Aug. 14, 1998 (CA) .............................................. 2245224

(51) Int. Cl.$^7$ .......................... C07K 7/00; C07K 7/02; C07K 7/04; A61K 38/21; A01N 61/00
(52) U.S. Cl. ......................... 514/15; 424/85.4; 514/2; 514/16; 530/300; 530/323; 530/328
(58) Field of Search ............................ 424/85.4; 514/2, 514/15, 16; 530/300, 323, 328, 332

(56) References Cited

U.S. PATENT DOCUMENTS

| | | |
|---|---|---|
| 2,530,369 A | 11/1950 | Simons et al. |
| 2,760,992 A | 8/1956 | Schoeffel et al. |
| 4,554,101 A | 11/1985 | Hopp et al. |
| 5,807,744 A | 9/1998 | Berneman et al. |
| 5,856,301 A | 1/1999 | Craig et al. |
| 5,919,776 A | 7/1999 | Hagmann et al. |

(Continued)

FOREIGN PATENT DOCUMENTS

| | | |
|---|---|---|
| WO | WO 98/04698 | 2/1998 |
| WO | WO 00/09152 | 2/2000 |

OTHER PUBLICATIONS

Wells (Sep. 18, 1990) "Additivity of Mutational Effects in Proteins." Biochemistry 29(37): 8509–8517.*

(Continued)

*Primary Examiner*—Elizabeth Kemmerer
*Assistant Examiner*—Christopher James Nichols
(74) *Attorney, Agent, or Firm*—Townsend and Townsend and Crew LLP

(57) ABSTRACT

The invention provides a variety of therapeutic uses for CXCR4 antagonists. In various embodiments. CXCR4 antagonsits may be used as therapeutically as follows, or to manufacture a medicament for such therapeutic treatments: reducing interferon gamma production by T-cells, treatment of an autoimmune disease, treatment multiple sclerosis, treatment of cancer, inhibition of angiogenesis. The invention provides corresponding methods of medical treatment, in which a therapeutic dose of a CXCR4 antagonist is administered in a pharmacologically acceptable formulation. Accordingly, the invention also provides therapeutic compositions comprising a CXCR4 antagonist and a pharmacologically acceptable excipient or carrier. The CXCR4 antagonists for use in the invention may be peptide compounds comprising a substantially purified peptide fragment, modified fragment, analogue or pharmacologically acceptable salt of SDF-1.

20 Claims, 14 Drawing Sheets

```
      Lys  Gly  Val  Ser  Leu  Ser  Tyr  Arg
                                           |
                                           X
                                           |
      Lys  Gly  Val  Ser  Leu  Ser  Tyr  Arg

Lys  Gly  Val  Ser  Leu  Ser  Tyr  Arg  Cys
                                           |
                                           X
                                           |
 Lys  Gly  Val  Ser  Leu  Ser  Tyr  Arg  Cys
```

U.S. PATENT DOCUMENTS

| | | | |
|---|---|---|---|
| 5,962,462 A | 10/1999 | Mills et al. | |
| 5,990,163 A | 11/1999 | Evans et al. | |
| 6,013,644 A | 1/2000 | Mills et al. | |
| 6,022,848 A | 2/2000 | Kozlov et al. | |
| 6,046,185 A | 4/2000 | Burgoyne et al. | |
| 6,124,319 A | 9/2000 | MacCoss et al. | |
| 6,132,987 A | 10/2000 | Charo et al. | |
| 6,133,319 A | 10/2000 | Widdowson et al. | |
| 6,136,827 A | 10/2000 | Caldwell et al. | |
| 6,140,349 A | 10/2000 | Caldwell et al. | |
| 6,166,037 A | 12/2000 | Budhu et al. | |
| 6,204,294 B1 | 3/2001 | Bryan et al. | |
| 6,613,742 B1 * | 9/2003 | Huang et al. | 514/12 |
| 2002/0156034 A1 * | 10/2002 | Tudan et al. | 514/44 |
| 2003/0202963 A1 * | 10/2003 | Crystal et al. | 424/93.2 |

OTHER PUBLICATIONS

Ngo et al. (Mar. 2, 1995) "The Protein Folding Problem and Tertiary Structure Prediction, Chapter 14: Computational Complexity Protein Structure Prediction, and the Levinthal Paradox" pp. 433–506.*

Bork (2000) "Powers and Pitfalls in Sequence Analysis: The 70% Hurdle." Genome Research 10:398–400.*

Skolnick and Fetrow (2000) "From gene to protein structure and function: novel applications of computational approaches in th genomic ara." Trends in Biotech. 18(1): 34–39.*

Doerks et al. (Jun. 1998) "Protein annotation: detective work for function prediction." Trends in Genetics 14(6): 248–250.*

Smith and Zhang (Nov. 1997) "The challenges of genome sequence annotation or 'The devil is in the details'." Nature Biotechnology 15: 1222–1223.*

Brenner (Apr. 1999) "Errors in genome annotation." Trends in Genetics 15(4): 132–133.*

Bork and Bairoch (Oct. 1996) "Go hunting in sequence databases but watch out for the traps." Trends in Genetics 12(10): 425–427.*

Heveker et al. (Mar. 26, 1998) "Dissociation of the signalling and antiviral properties of SDF–1–derived small peptides." Curr Biol. 8(7): 369–376.*

Acsadi, G. et al, "Human Dystrophin Expression in MDX Mice After Intramuscular Injection of DNA Constructs" (1991) Nature vol. 352, 815–818.

Alkhatib, G. et al, "CC CKR5: A RANTES, MIP–1α, MIP–β, Receptor as a Fusion Cofactor for Macrophage–Tropic HIV–1" (1996) Science vol. 272, 1955–1958.

Allen, M. et al, "High Throughput Fluorescence Polarization: A Homogeneous Alternative to Radioligand Binding for Cell Surface Receptors" (2000) J. Biomolecular Screening vol. 5 No. 2, 63–69.

Anderlini, P. et al., "Allogenic Blood Stem Cell Transplantation: Considerations for Donors" (1997) Blood vol. 90 No. 3, 903–908.

Anderson, W. et al, "The Best of Times, the Worst of Times" (2000) Science vol. 288, 627–629.

Arenzana–Selsdedos, F. et al, "HIV Blocked by Chemokine Antagonist" (1996) Nature vol. 383, 400.

Avenarius, H. et al, "Granulocyte Colony–stimulating Factor Enhances the Expression of CD62 on Platelets in vivo" (1993) Inter. J. Hematology vol. 58, 189–196.

Baggiolini, M. "Chemokines and Leukocyte Traffic" (1998) Nature vol. 392, 565–568.

Barbier, J. et al, "Bioactivities and Secondary Structures of Constrained Analogues of Human Parathyroid Hormone: Cyclic Lactams of the Receptor Binding Region" (1997) J. Med. Chem. vol. 40 No. 9, 373–1380.

Barbier, J. et al, "Structure and Activities of Constrained Analogues of Human Parathyroid Hormone and Parathyroid Hormone–Related Peptide: Implications for Receptor–Activting Conformtations of the Hormones" (2000) Biochemistry 2000 vol. 39 No. 47, 14522–14530.

Barnes, D. et al, "Polyclonal Antibody Directed Against Human RANTES Ameliorates Disease in the Lewis Rat Adjuvant–Induced Arthritis Model" (1998) J. Clin. Invest. vol. 101 No. 12., 2910–2919.

Blease, K. et al, "Airway Remodeling is Absent in CCR1−/− Mice During Chronic Fungal Allergic Airway Disease" (2000) J. Immunol. vol. 165, 1564–1572.

Brandt, J. et al, "Cytokine–dependent Long–Term Culture of Highly Enriched Precursors of Hematopoietic Progenitor Cells from Human Bone Marrow" (1990) J. Clin. Invest., vol. 86, 932–941.

Brandt, J. et al, "Role of c–kit Ligand in the Expansion of Human Hematopoietic Progenitor Cells" (1992) Blood vol. 79 No. 3, 634–641.

Brandt, J. et al, "Characterization of a Human Hematopoietic Progenitor Cell Capable of Forming Blast Cell Containing Colonies in vitro" (1998) J. Clin. Invest. vol. 82, 1017–1027.

Buckley, C. et al, "Persistent Induction of the Chemokine Receptor CXCR4 by TGF–β1 on Synovial T Cells Contributes to Their Acumulation within the Rheumatoid Synovium" (2000) J. Immunol. vol. 165, 3423–3429.

Burt, R., "Hematopoietic Stem Cell Transplantation: A New Therapy for Autoimmune Disease" (1999) Stem Cells vol. 17, No. 6, 366–372.

Campbell, J. et al, "Chemokines and the Arrest of Lymphocytes Rolling Under Flow Conditions" (1998). Science vol. 279, 381–383.

Cashman, J. et al, "Differentiation Stage–Specific Regulation of Primitive Human Hematopoietic Progenitor Cycling by Exogeneous and Endogeneous Inhibitors in an in Vivo Model" (1999) Blood vol. 94 No. 11, 3722–3729.

Cavazzana–Calvo, M. et al, "Gene Therapy of Human Severe Combined Immunodeficiency (SCID)–X1 Disease" (2000) Science vol. 288, 669–672.

Charo, O. et al, "Molecular Cloning and Functional Expression of Two Monocyte Chemoattractant Protein 1 Receptors Reveals Alternative Splicing of the Carboxyl–terminal Trails" (1994) Proc. Natl. Acad. Sci. vol. 91, 2752–2756.

Choe, H. et al, "The β–Chemokine Receptors CCR3 and CCR5 Facilitate Infection by Primary HIV–1 Isolatas" (1996) Cell vol. 85, 1135–1148.

Clapp, W. et al, "Fetal Liver Hematopoietic Stem Cells as a Target for In Utero Retroviral Gene Transfer" (1991) Blood vol. 78 No. 4, 1132–1139.

Combadiere, C. et al, "Cloning and Functional Expression of a Human Eosinophil CC Chemokine Receptor" (1995) J. Biol. Chem. vol. 270, 16491–16494.

Conti, J. et al, "Acute Arterial Thrombosis After Escalated–Dose Methotrexate, Vinoblastine, Doxorubicin, and Cisplatin Chemotherapy with Recombinant Granulocyte Colony–Stimulating Factor" (1992) Cancer vol. 70 No. 11, 2699–2702.

Cushing, S. et al, "Minimally Modified Low Density Lipoprotein Induces Monocyte Chemotactic Protein 1 in Human Endothelial Cells and Smooth Muscle Cells" (1990) *Proc. Natl. Acad. Sci.* vol. 87, 5234–5138.

Demirer, T. et al, "Optimization of Peripheral Blood Stem Cell Mobilization" (1996) *Stem Cells* vol. 14, 106–116.

Deng, H. et al, "Identification of a Major Co–receptor for Primary Isolates of HIV–1". (1996) *Nature* vol. 381, 661–666.

Di Salvo, J. et al, "The CXCR4 Agonist Ligand Stromal Derived Factor–1 Maintains High Affinity for Receptors in Both $G_{ai}$—coupled and Uncoupled States" (2000) *Eur. J. Pharm.* vol. 409, 143–154.

Doranz, B. et al "A Dual–Tropic Primary HIV–1 Isolate that Uses Fusin and the β–Chemokine Receptors CKR–5, CKR–3, and CKR–2b as Fusion Cofactors" (1996) *Cell* vol. 85, 1149–1158.

Dragic, T. et al, "HIV–1 Entry into $CD4^+$ Cells is Mediated by the Chemokine Receptor CC–CKR–5" (1996) *Nature* vol. 381, 667–673.

Dunican, A. et al, "CXC Chemokine Suppression of Polymorphonuclear Leukocytes Apoptosis and Preservation of Function is Oxidative Stress Independent" (2000) *Shock* vol. 13 No. 3, 244–250.

Durig, J. et al, "Biological Effects of Stroma–derived Factor–1α on Normal and CML $CD34^+$ Haemopoietic Cells" (2000) *Leukemia* vol. 14, 1652–1660.

Elisseeva, E. et al, "NMR Studies of Active N–terminal Peptides of Stromal Cell–derived Factor–1" (2000) *J. Biol. Chem.* vol. 275 No. 35, 26799–26805.

Elseviers, M. et al, "Evidence for the Bioactive Conformation in a Cyclic Hexpapetide Analogue of Somatostatin Containign a CIS–Peptide Bond Mimic" (1998) *Biochem. and Biophys. Research Comm.* vol. 154 No. 2, 515–521.

Fletcher, F. et al, "Murine Leukemia Inhibitory Factor Enhances Retroviral–Vector Infection Efficiency of Hematopoietic Progenitors" (1990) *Blood* vol. 76 No. 6, 1098–1103.

Furuichi, K. et al, "Distinct Expression of CCR1 and CCR5 in Glomerular and Interstitial Lesions of Human Glomerular Diseases" (2000) *Am. J. Nephrol.* vol. 20, 291–299.

Gimbrone, M. et al, "Endothelial Interleukin–8: A Novel Inhibitor of Leukocyte–Endothelial Interactions" (1989) *Science* vol. 246, 1601–1603.

Giralt, S. et al, "Engraftment of Allogeneic Hematopoietic Progenitor Cells with Purine Analog–Containing Chemotherapy: Hamessing Graft–Versus Host Leukemia Without Myeloablative Therapy" (1997) *Blood* vol. 89 No. 12, 4531–4536.

Haas, R. et al, "Recombinant Human Granulocyte–Macrophage Colony–stimulating Factor (rhGM–CSF) Subsequent to Chemotherapy Improves Collection of Blood Stem Cells for Autografting in Patients not Eligible for Bone Marrow Harvest" (1992) *Bone Marrow Transplantation* vol. 9, 459–465.

Hamada, T. et al, "Transendothelial Migration of Megakaryocytes in Response to Stromal Cell–derived Factor 1 (SDF–1) Enhances Platelet Formation" (1998) *J. Exp. Med.* vol. 188 No. 3, 539–548.

Ho, A. et al, "Optimal Timing for Collections of Blood Progenitor Cells Following Induction Chemotherapy and Granulocyte–Macrophage Colony–Stimulating Factor for Autologous Transplantation in Advanced Breast Cancer" (1993) *Leukemia*, vol. 7 No. 11, 1738–1746.

Holmes, W. et al, "Structure and Function Expression of a Human Interleukin–8 Receptor" (1991) *Science* vol. 253 No. 50, 1278–1280.

Horuk, R. et al, "A Non–peptide Functional Antagonist of the CCR1 Chemokien Receptor is Effective in Rat Heart Transplant Rejection" (2001) *J. Biol. Chem.* vol. 276 No. 6, 4199–4204.

Huang, S. et al, "Formation of Haematopoietic Microenvironment and Haematopoietic Stem Cells from Single Human Bone Marrow Stem Cells" (1992) *Nature* vol. 360, 745–749.

Huber, A. et al, "Regulation of Transendothelial Neutrophil Migration by Endogenous Interleukin–8" (1991) *Science* vol. 254, 99–102.

Ikebuchi, K. et al, "Granulocyte Colony–Stimulating Factor Enhances Interleukin 3–Dependent Proliferation of Multipotential Hemopoietic Progenitors" (2001) *Nat. Acad. Sci.* vol. 85, No. 10, 3445–3449.

Imai, T. et al, "The T Cell–directed CC Chemokine TARC is a Highly Specific Biological Ligand for CC Chemokine Receptor 4" (1997) *J. Biol. Chem.* vol. 272 No. 23, 15036–15042.

Imai, T. et al, "Macrophage–derived Chemokines is a Functional Ligand for the CC Chemokine Receptor 4"(1998) *J. Biol. Chem.* vol. 273 No. 3, 1764–1768.

Kates, S. et al, "Automated Allyl Cleavage for Continuous–Flow Synthesis of Cyclic and Branched Peptides" (1993) *Analytical Biochemistry* vol. 212, 303–310.

Kawachi, Y. et al, "Acute Arterial Thrombosis due to Platelet Aggregation in a Patient Receiving Granyulocyte Colony–Stiimulating Factor" (1996) *Brit. J. Hematology* vol. 94, 413–416.

Kim, C. et al, "Chemokines: Signal Lamps for Trafficking of T and B Cells for Development and Effector Function" (1999) *J. Leukocyte Biology* vol. 65, 6–15.

Kitaura, M. et al, "Molecular Cloning of Human Eotaxin, an Eosinophil–selective CC Chemokine, and Identification of a Specific Eosinophil Eotaxin Receptor, CC Chemokine Receptor 3" (1996) *J. Biol. Chem.* vol. 271 No. 13, 7725–7730.

Koch, A. et al, "Interleukin–8 as a Macrophage–Derived Mediator of Angiogenesis" (1992) *Science* vol. 258, 1798–1801.

Kowalska, M. et al, "Stromal Cell–derived Factor–1 and Macrophage–derived Chemokine: 2 Chemokines that Activate Platelets" (2000) *Blood* vol. 96, No. 1, 50–57.

Kramer, W. et al, "Liver–specific Drug Targeting by Coupling to Bile Acids" (1992) *J. Biol. Chem.* vol. 267 No. 26, 18598–18604.

Kume, A. et al, "Hematopoietic Stem Cell Gene Therapy: A Current Overview" (1999) *Int. J. Hematology* vol. 69, 227–233.

Kuroiwa, M. et al, "Effects of Granulocute Colony–stimulating Factor on the Hemostatic System in Healthy Volunteers" (1996) *Int. J. Hematology*, vol. 63, 311–316.

Lasky, L. et al, "Donor Platelet Response and Product Quality Assurance in Plateletpheresis" (1981). *Transfusion* vol. 21 No. 3, 247–260.

Law, P., "The Tolerance of Human Platelets to Osmotic Stress" (1983) *Exp. Hematol.* vol. 11 No. 5, 351–357.

Le Chevalier, T., "Dose Optimisation and Intensificaiton of Cytotoxics in Solid Tumours Supported by Haematopoietic Growth Factors" (1994) *Eur. J. Cancer* vol. 30A No. 3, 410–412.

Leary, A. et al, "Synergism Between Interleukiun–6 and Interleukin–3 in Supporting Proliferation of Human Hematopoietic Stem Cells: Comparison with Interleukin–1α" (1988) *Blood* vol. 71 No. 6, 1759–1763.

Lemarchand, P. et al, "Adenovirus–mediated Transfer of a Recombinant Human $α_1$– antitrypsin cDNA to Human Endothelial Cells" (1992) *Nat. Acad. Sci.* vol. 89 No. 4, 6482–6486.

Lin, T. et al, "Human Mast Cells Transmigrate Through Human Umbilical Vein Endothelial Monolayers and Selectively Produce IL–8 in Response to Stromal Cell–Derived Factor–1α" (2000) *J. Immunol.* vol. 165, 211–220.

Lohrmann, H. et al, "Changes of Granulopoiesis During and After Adjuvant Chemotherapy of Breast Cancer" (1978) *B. J. Haematol.* vol. 40, 369–381.

Lombart, H. et al, "Synthesis of Enantiopure α,ω–Diamino Dicarboxylates and Azabicycloalkane Amino Acids by Claisen Condensation of α–[N–(Phenylfluorenyl)amino] Dicarboxylates" (1994) J. Org. Chem. vol. 59, 6147–6149.

Lukacs, N. et al, "Differential Recruitment of Leukocyte Populations and Alteration of Airway Hyperreactivity by C–C Family Chemokines in Allergic Airway Inflammation" (1997) *J. Immunol* vol. 158, 4398–4404.

Luo, J. et al, "Attachment of C–Terminus of SDF–1 Enhances the Biological Activity of its N–Termianl Peptide" (1999) *Biochemical and Biophysical Research Communications* vol. 264, 42–47.

Marshall, G. et al, "A Heirarachial Approach to Peptidomimetic Design" (1993) *Tetrahedron* vol. 49 No. 17, 3547–3558.

Moss, T. et al, "Contamination of Peripheral Blood Stem Cell Harvests by Circulating Neuroblastoma Cells" (1990) *Blood* vol. 76 No. 9, 1879–1883.

Murphy, P. et al, "Cloning of Complementary DNA Encoding a Functional Human Interleukin–8 Receptor" (1991) *Science* vol. 258, 1280–1283.

Myers, S. et al, "Signal Transduction and Ligand Specificity of the Human Monocyte Chemoattractant Protein–1 Receptor in Transfected Embryonic Kidney Cells" (1995) *J. Biol. Chem.* vol. 270 No. 11, 5786–5792.

Nagai, U. et al, "Bicyclic Turned Dipeptide (BTD) as a β–turn Mimetic; its Design, Synthesis and Incorporation into Bioactive Peptides" (1993) *Tetrahedron* vol. 49 No. 17, 3577–3592.

Nagasawa, T. et al, "Molecular Cloning and Structure of a Pre–B–Cell Growth Stimulting Factor" (1994) *Proc. Natl. Acad. Sci.* vol. 91, 2305–2309.

Neole, K. et al, "Molecular Cloning, Functional Expression, and Signaling Characteristics of a C–C Chemokine Receptor" (1993) *Cell* vol. 72, 415–425.

Ng, H. et al, "Discovery of Novel Non–peptide CCR1 Receptor Antagonists" (1999) *J. Med. Chem.* vol. 42, 4680–4694.

Pettengell, R. et al, "Transplantation Potential of Hematopoietic Cells Released into the Circulation During Routine Chemotherapy for Non–Hodgkin's Lymphoma" (1993) *Blood* vol. 82 No. 7, 2239–2248.

Richman, C. et al, "Increase in Circulating Stem Cells Following Chemotherapy in Man" (1976) *Blood* vol. 47 No. 6, 1031–1039.

Richmond, A. et al, "Purification of Melanoma Growth Stimulatory Activity" *J. Cell Phys.* vol. 129, 375–384.

Ripka, W. et al, "Protein β–Turn Mimetics I. Design, Synthesis, and Evaluation in Model Cyclic Peptides" (1993) *Tetrahedron* vol. 49 No. 17, 3593–3608.

Sabers, A., et al, "Cognitive Function and Anticonvulsant Therapy: Effect of Monotherapy in Epilepsy" (1995) *Acta. Neurol. Scand.* vol. 92, 19–27.

Schiffer, C. et al, "Platelet Cryopreservation Using Dimethyl Sulfoxide" (1983) *Ann. N.Y. Acad. Sci.*, 161–169.

Shimoda, K. et al, "Identification of a Functional Receptor for Granulocyte Colony–Stimulating Factor on Platelets" (1993) *J. Clin. Invet.* vol. 91 No. 4, 1310–1313.

Siena, S. et al, "Circulation of $CD34^+$ Hematopoietic Stem Cells in the Peripheral Blood of High–Dose Cyclophosphamide–Treated Patients: Enhancement by Intravenous Recombinant Human Granulocyte–Macrophage Colony––Stimulating Factor" (1989) *Blood* vol. 74 No. 6, 1905–1914.

Stiff, P. et al, "Quantification of the Peripheral Blood Colony Forming Unit–Culture Rise Following Chemotherapy" (1983) *Transfusion* vol. 23, 500–503.

Strieter, M. et al, "Endothelial Cell Gene Expresion of a Neutrophil Chemotactic Factor by TNF–α , LPS, and IL–1β" (1989) *Science* vol. 253, 1467–1469.

Strieter, R. et al, "Monokine–Induced Neutrophil Chemotactic Factor Gene Expression in Human Fibroblasts" (1989) *J. Biol. Chem.* vol. 264 No. 18, 10621–10626.

Tashiro, K. et al, "Signal Sequence Trap: A Cloning Strategy for Secreted Proteins and Type I Membrane Protein" (1993) *Science* vol. 261, 600–603.

Thelari, M. et al, "Mechanism of Neutrophil Activation by NAF, a Novel Monocyte–derived Peptide Agonist" (1986) *FASEB J.* vol. 2, 2702–2706.

To, L et al, "Comparison of Haematological Recovery Times and Supportive Care Requirements of Autologous Recovery Phase Peripheral Blood Stem Cell Transplants, Autologous Bone Marrow Transplants and Allogenic Bone Marrow Transplants" (1992) *Bone Marrow Transplantation* vol. 9, 277–284.

Tokuda, A. et al, "Pivotal Role of CCR–1 Positive Leukocytes in Bleomycin–Induced Lung Fibrosis in Mice" (2000) *J. Immunol.* vol. 164, 2745–2751.

Tsuji, T. et al, "Molecular Cloning of the Large Subunit of Transforming Growth Factor Type β Masking Protein and Expression of the mRNA in Various Rat Tissues" (1990) *Proc. Natl. Acad. Sci.* vol. 87, 8835–8839.

Unemori, E. et al, "Melanoma Growth–Stimulatory Activity/GRO Decreases Collagen Expression by Human Fibroblasts" (1992) *J. Biol. Chem* vol. 268 No. 2, 1338–1342.

Verfaillie, C. et al, "Purified Primitive Human Hematopoietic Progenitor Cells with Long–Term in Vitro Repopulating Capacity Adhere Selectively to Irradiated Bone Marrow Stroma" (1990) *J. Exp. Med.* vol. 172, 509–520.

Wang, J. et al, "The α–Chemokine Receptor CXCR4 is Expressed on the Megakaryocytic Lineage From Progenitor to Platelets and Modulates Migration and Adhesion" (1998) *Blood* vol. 92 No. 3, 756–764.

Warringa, R. et al, "Modulation and Induction of Eosinophil Chemotaxis by Granulocyte–Macrophage Colony–Stimulting Factor and Interleukin–3"(1991) *Blood* vol. 77 No. 12, 2694–2700.

Wess, G. et al, "Modified Bile Acids: Preparation of 7α, 12α–Dihydroxy–3β–and 7α, 12α–Dihydroxy–3α–(2–Hydroxyethoxy)–5β–Cholanic Acid and their Biological Activity" (1992) *Tetrahedron Letters* vol. 33 No. 2, 195–198.

Wess, G. et al, "Preparation of 3α–and 3β–(ω–aminoalkoxy)– 7α, 12α,Dihydroxy–5β–Cholanoic Acid Esters: Versatile Shuttles for Drug Targeting" (1993) *Tetrahedron Letters*, vol. 34 No. 5, 817–818.

Wu., G. et al, "Receptor–mediated Gene Delivery and Expression in vivo" (1988) *J. Biol. Chem.* vol. 263 No. 29, 14621–14624.

Ying, S. et al, "Eosinophl Chemotactic Chemokines (Eotaxin, Eotaxin–2, RANTES, Monocyte Chemoattractant Protein–3 (MCP–3), and (MCP–4), and C–C Chemokine Receptor 3 Expression in Bronchial Biopsies from Atopic and Nonatopic (Intrinsic) Asthmatics" (1999) *J. Immunol.* vol. 163, 6321–6329.

Yla–Herttuala, S. et al, "Expression of Monocyte Chemoattactant Protein 1 in Macrophage–rich Areas of Human and Rabbit Atherosclerotic Lesions" (1991) *Proc. Natl. Acad. Sci.* vol. 88, 5252–5256.

Zhou, N. et al, "A Novel Peptide Antagonist of CXCR4 Derived from the N–Terminus of Viral Chemokine vMIP–II" (2000) *Biochemistry 2000*, vol. 39, 3782–3787.

Zsebo, K. et al, "Identification, Purification, and Biological Characterization of Hematopoetic Stem Cell Factor from Buffalo Rat Liver–Conditioned Medium" (1990) *Cell* vol. 63, 195–201.

* cited by examiner

SDF-1α

```
         1          11         21
         |          |          |
         KPVSLSYRCP CRFFESHVAR ANVKHLKILN 31         41         51
         |          |          |
         TPNCALQIVA RLKNNNRQVC IDPKLKWIQE

61
         |
         YLEKALN
```

SDF-1β

```
         1          11         21
         |          |          |
         KPVSLSYRCP CRFFESHVAR ANVKHLKILN 31         41         51
         |          |          |
         TPNCALQIVA RLKNNNRQVC IDPKLKWIQE 61         71
         |          |
         YLEKALNKRF KM
```

Figure 1 a
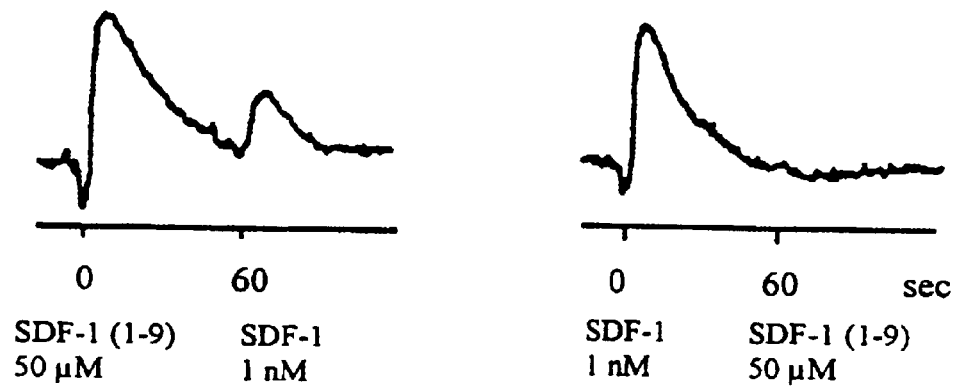
b
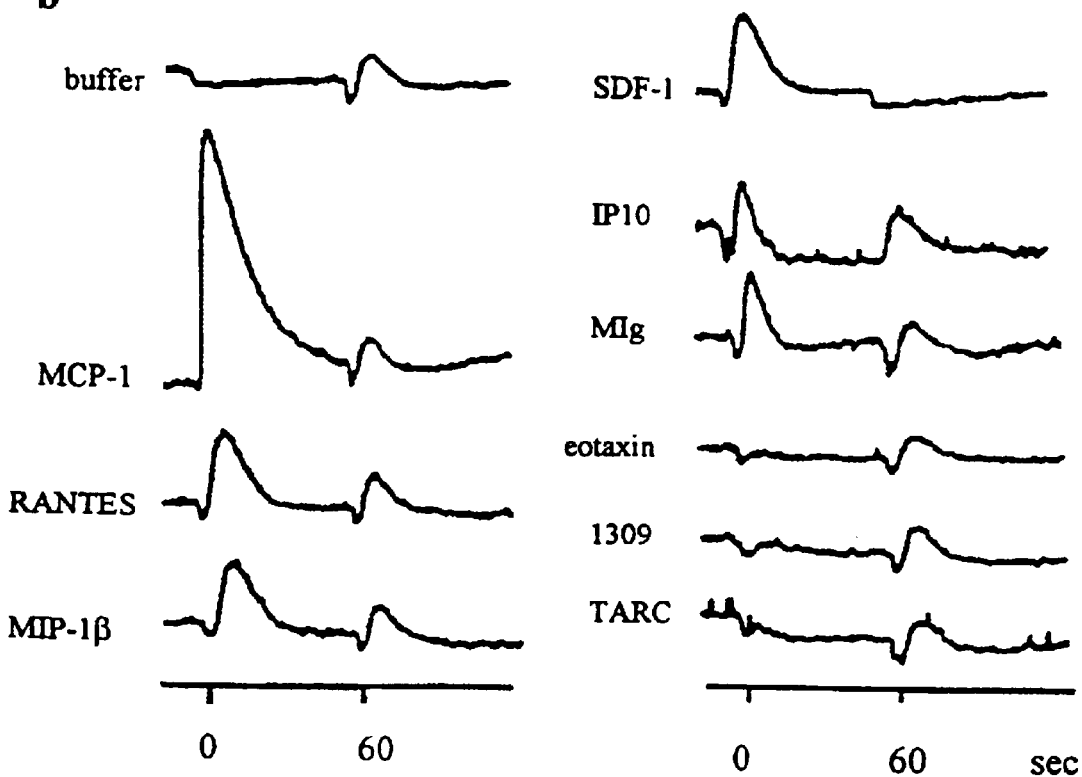
Figure 5

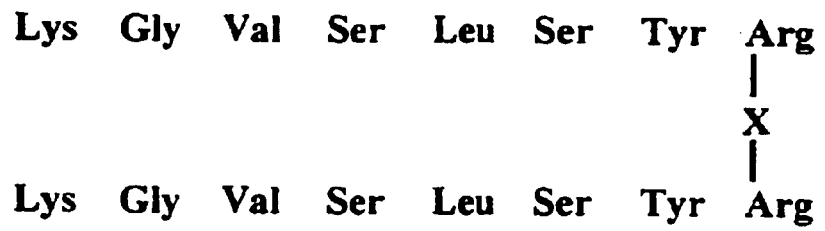
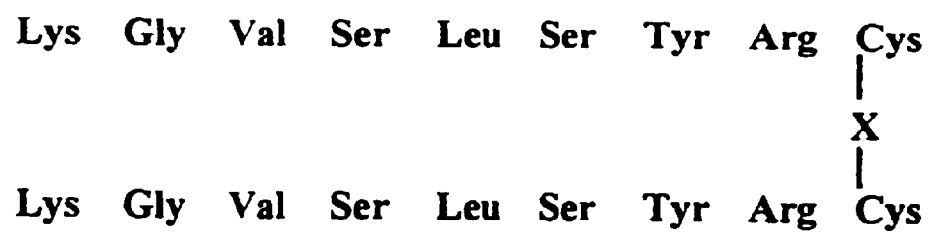
Figure 14

THERAPEUTIC CHEMOKINE RECEPTOR ANTAGONISTS

FIELD OF THE INVENTION

The invention relates to the therapeutic uses of chemokine receptor antagonists, including peptide antagonists of CXC chemokine receptor 4 for use in the treatment of cancer and autoimmune disease.

BACKGROUND OF THE INVENTION

Cytokines are soluble proteins secreted by a variety of cells including monocytes or lymphocytes that regulate immune responses. Chemokines are a superfamily of chemoattractant proteins. Chemokines regulate a variety of biological responses and they promote the recruitment of multiple lineages of leukocytes and lymphocytes to a body organ tissue. Chemokines may be classified into two families according to the relative position of the first two cysteine residues in the protein. In one family, the first two cysteines are separated by one amino acid residue, the CXC chemokines, and in the other family the first two cysteines are adjacent, the CC chemokines.

The molecular targets for chemokines are cell surface receptors. One such receptor is CXC chemokine receptor 4 CXCR4), which is a 7 transmembrane protein, coupled to G1 and was previously called LESTR (Loetscher, M., Geiser, T., O'Reilly, T., Zwahlen, R., Baggionlini, M., and Moser, B., (1994) J. Biol. Chem, 269, 232–237). HUMSTR (Federsppiel, B., Duncan, A. M. V., Delaney, A., Schappert, K., Clark-Lewis, I., and Jirik, F. R. (1993) Genomics 16, 707–712) and Fusin (Feng, Y., Broeder, C. C., Kennedy, P. E., and Berger, E. A. (1996) HIV-1 entry cofactor: Functional cDNA cloning of a seven-transmembrane G protein-coupled receptor, Science 272, 872–877). CXCR4 is widely expressed on cells of hemopoietic origin, and is a major co-receptor with CD4 for human immunodeficiency virus 1 (HIV-1) (Feng, Y., Broeder, C. C., Kennedy, P. E., and Berger, E. A. (1996) HIV-1 entry cofactor: Functional cDNA cloning of a seven-transmembrane G protein-coupled receptor, Science 272, 872–877).

Currently, the only known natural ligand for CXCR4 is stromal cell derived factor one (SDF-1). Stromal cell derived factor-1α (SDF-1α) (SEQ ID NO: 6) and stromal cell derived factor-1β (SDF-1β) (SEQ ID NO: 7) are closely related members (together referred to herein as SDF-1). The native amino acid sequences of SDF-1α and SDF-1β are known, as are the genomic sequences encoding these proteins (U.S. Pat. No. 5,563,048 issued 8 Oct. 1996, and U.S. Pat. No. 5,756,084 issued 26 May 1998).

SDF-1 is functionally distinct from other chemokines in that it is reported to have a fundamental role in the trafficking, export and homing of bone marrow progenitor cells (Aiuti, A., Webb, I. J., Bleul, C., Springer, T., and Guierrez-Ramos, J. C. (1996) J. Exp. Med. 185, 111–120 and Nagasawa, T., Hirota, S., Tachibana, K., Takakura N., Nishikawa, S. -I., Kitamura, Y., Yoshida, N., Kikutani, H., and Kishimoto, T., (1996) Nature 382, 635–638). SDF-1 is also structurally distinct in that it has only about 22% amino acid sequence identity with other CXC chemokines (Bleul, C. C., Fhulbrigge, R. C., Casasnovas, J. M., Aiuti, A., and Springer, T. A., (1996) J. Exp. Med, 184 1101–1109). SDF-1 appears to be produced constitutively by several cell types, and particularly high levels are found in bone-marrow stromal cells (Shirozu, M., Nakano, T., Inazawa, J., Tashiro, K., Tada, H. Shinohara, T., and Honjo, T., (1995) Genomics, 28, 495–500 and Bleul, C. C., Fuhlbrigge, R. C., Casasnovas, J. M., Aiuti, A., and Springer, T. A., (1996) J. Exp. Med. 184, 1101–1109). A basic physiological role for SDF-1 is implied by the high level of conservation of the SDF-1 sequence between species. In vitro, SDF-1 stimulates chemotaxis of a wide range of cells including monocytes and bone marrow derived progenitor cells (Aiuti, A., Webb, I. J., Bleul, C., Springer, T., and Guierrez-Ramos, J. C., (1996) J. Exp. Med. 185, 111–120 and Bleul, C. C., Fuhlbrigge, R. C., Casasnovas, J. M., Aiuti, A., and Springer, T. A., (1996) J. Exp. Med. 184, 1101–1109). Particularly notable is its ability to stimulate a high percentage of resting and activated T-lymphocytes (Bleul, C. C., Fhulbrigge, R. C., Casasnovas, J. M. Aiuti, A., and Springer, T. A., (1996) J. Exp. Med. 184, 1101–1109 and Campbell, J. J., Hendrick, J., Zlotnik, A., Siani, M. A., Thompson, D. A., and Butcher, E. C., (1998) Science, 279 381–383).

The 3-dimensional crystallographic structure of SDF-1 has been described (Crump, M., Gong J. -H, Loetscher, P., Rajarathnam, K., Amara, A., Arenzana-Seisdedos, F., Virelizier, J. -L., Baggiolini, M., Sykes, B. D., and Clark-Lewis, I., (1997) EMBO J., 16, 6996–7007). Structure-activity analysis of SDF-1 (Crump, M., Gong J. -H., Loetscher, P., Rajarathnam, K., Amara, A., Arenzana-Seisdedos, F., Virelizier, J. -L., Baggiolini, M., Sykes, B. D., and Clark-Lewis, I., (1997) EMBO J., 16, 6996–7007) indicates that although N-terminal residues 1–8 or 1–9 are involved in receptor binding, the 1–8 and 1–9 peptides alone exhibited no in vitro activity indicative of receptor binding, supporting a reported conclusion that the peptides do not assume the conformation necessary for binding to the receptor. This result was taken to imply that the remainder of the protein scaffold, and/or various consensus receptor binding sites elsewhere in the protein are important for mediating the conformational requirements for N-terminal binding to the receptor (Crump, M., Gong J. -H., Loetscher, P., Rajarathnam, K., Amara, A., Arenzana-Seisdedos, F., Virelizier, J. -L., Baggiolini, M., Sykes, B. D., and Clark-Lewis, I., (1997) EMBO J., 16, 6996–7007). Based on these results, a two-site model has been proposed for SDF-1 binding to CXCR4, involving two binding sites in residues 1–17, an N-terminal siteand an upstream RFFESH (SEQ ID NO:5) site (Crump, M., Gong J. -H., Loetscher, P., Rajarathnam, K., Amara, A., Arenzana-Seisdedos, F., Virelizier, J. -L., Baggiolini, M., Sykes, B. D., and Clark-Lewis, I., (1997) EMBO J., 16, 6996–7007). The two putative binding sites are joined by the CXC motif that characterizes the whole CXC chemokine family (Crump, M., Gong J. -H., Loetscher, P., Rajarathnam, K., Amara, A., Arenzana-Seisdedos, F., Vireliziers, J. -L., Baggiolini, M., Sykes, B. D., and Clark-Lewis, I., (1997) EMBO J., 16, 6996–7007). These two putative binding regions have been identified as being important in other CC and CXC chemokines (Crump, M., Gong J. -H., Loetscher, P., Rajarathnam, K., Amara, A., Arenzana-Seisdedos, F., Virelizier, J. -L., Baggiolini, M., Sykes, B. D., and Clark-Lewis, I., (1997) EMBO J., 16, 6996–7007). This is consistent with the finding that although N-terminal regions of a wide variety of chemokines are critical for receptor activations, N-terminal peptides of chemokines other than SDF-1 have been reported to lack receptor binding activity and not to be receptor agonists (Crump, M., Gong J. -H., Loetscher, P., Rajarathnam, K., Amara, A., Arenzana-Seisdedos, F., Virelizier, J. -L., Baggiolini, M., Sykes, B. D., and Clark-Lewis, I., (1997) EMBO J., 16, 6996–7007).

Consistent with the fact that CXCR4 is a major co-receptor for HIV-1, SDF-1 blocks HIV-1 entry into CD4 cells Oberlin, E., Amara, A., Bachelerie, F., Bessia, C., Virelizier, J. -L., Arenzana-Seisdedos, F., Schwartz, O., Heard, J. -M., Clark-Lewis, I., Legler, D. F., Loetscher, M., Baggiolini, M., and Moser, B., (1996) Nature, 382, 833–835 and Bleul, C. C., Farzan, M., Choe, H., Parolin, C., Clark-Lewis, I., Sodroksi, J., and Springer, T. A., (1996) Nature, 382, 829–833). Efforts have been made to identify SDF-1 derived peptides that interfere selectively with HIV entry, and not with SDF-1 signalling (Heveker, N. et al., 1988, Current Biology 8 (7):369–376). A wide range of potential CXCR4 binding fragments of SDF-1 have been proposed for use in blocking HIV infection (WO 9728258, published 7 Aug. 1997; WO 9804698, published 5 Feb. 1998). As these references make clear, the anti-HIV activity of SDF-1, or fragments of SDF-1, does not depend on antagonism of the CXCR4 receptor.

Interferon gamma is an important cytokine that is released by activated T-lymphocytes (T-cells) and acts as a potent immunomodulator. Interferon gamma production by T-cells in vivo may cause other cells in the body to release additional cytokines, enzymes and antibodies that are capable of modulating many aspects of an immune response. Agents which effect the ability of activated T-cells to produce interferon gamma are characterized as immunomodulators.

Autoimmune diseases are a group of illnesses generally understood to be caused by the over-production of cytokines, lymphotoxins and antibodies by white blood cells, including in particular T-cells. During an autoimmune reaction, T-cells are understood to release chemical mediators such as interferon gamma which lead to the development of pathological symptoms of autoimmune reaction. A treatment for autoimmune diseases may therefore involve the use of agents capable of inhibiting release of interferon gamma from T-cells. Such autoimmune diseases may include, for example, Multiple Sclerosis (MS), Guillain-Barre Syndrome, Amotrophic Lateral Sclerosis, Parkinson's disease, Alzheimer's disease, Gout, Lupus, and any other human illnesses that T-cells play a major role in.

Interferon beta is a cytokine that has found to have therapeutic application in the treatment of a variety of autoimmune diseases. In autoimmune diseases such as MS, the activation of Th1 type T-cells is thought to be a primary component of the autoimmune response. In MS, the autoimmune response attacks the myelin sheath neuronal axons. One of the classical markers of Th1 cell activation is the production of interferon gamma. In the development of interferon beta as a therapeutic agent for the treatment of MS, studies were conducted to demonstrate the ability of interferon beta to decrease the rate of production of interferon gamma from lymphocytes in vitro (Ann. Neurol, 1998; 44:27–34 and Neurology 1998; 50:1294–1300). The reduction of interferon gamma release by treatment with interferon beta is an indication of the effectiveness of interferon beta in the treatment of MS. There is a continuing need for other agents that inhibit the production of interferon gamma, particularly agents for use in the treatment of autoimmune disease, including agents that may work synergistically to enhance the effect of existing agents such as interferon beta.

Solid tumour growth is generally angiogenesis (neovascularization)-dependent, and angiogenesis, inhibitors have therefore been used as agents for the treatment of solid tumours and metastasis. Endothelial cells (EC) in the vasculature play an essential role in angiogenesis, and there is accordingly a need for therapeutic agents that target this activity. The proliferation, migration and differentiation of vascular endothelial cells during angiogenesis is understood to be modulated in both normal and disease states by the complex interactions of a variety of chemokines and chemokine receptors. CXCR4 is expressed on vascular EC, and in such cells is reportedly the most abundant receptor amongst all examined chemokine receptors (Gupta, et al, 1998).

BRIEF DESCRIPTION OF FIGURES

FIG. 1: Sequence of native SDF-1 (prior art). SDF-1α= SEQ ID NO:6; SDF-1β=SEQ ID NO:7.

FIG. 5: Receptor selectivity of the SDF-1 peptides. T-lymphocytes that were loaded with Fura-2 were sequentially stimulated with chemokines and SDF-1 (1–9) and the resulting $(Ca^{2+})_1$-dependent fluorescence changes were recorded. (a) Cross-desensitization of SDF-1 and the 1–9 peptide. (b) Lack of desensitization of SDF-1 (1–9) by the indicated CXC or CC chemokines. The chemokines were added at 100 nM, except for SDF-1 which was added at 1 nM, followed by addition of the 1–9 peptide (30 μM) after 60 s. The results shown are representative of two to three independent experiments.

FIG. 14: The structures of dimer peptide antagonist compounds (SEQ ID NOS:3 and 4).

SUMMARY OF THE INVENTION

Figure 2:
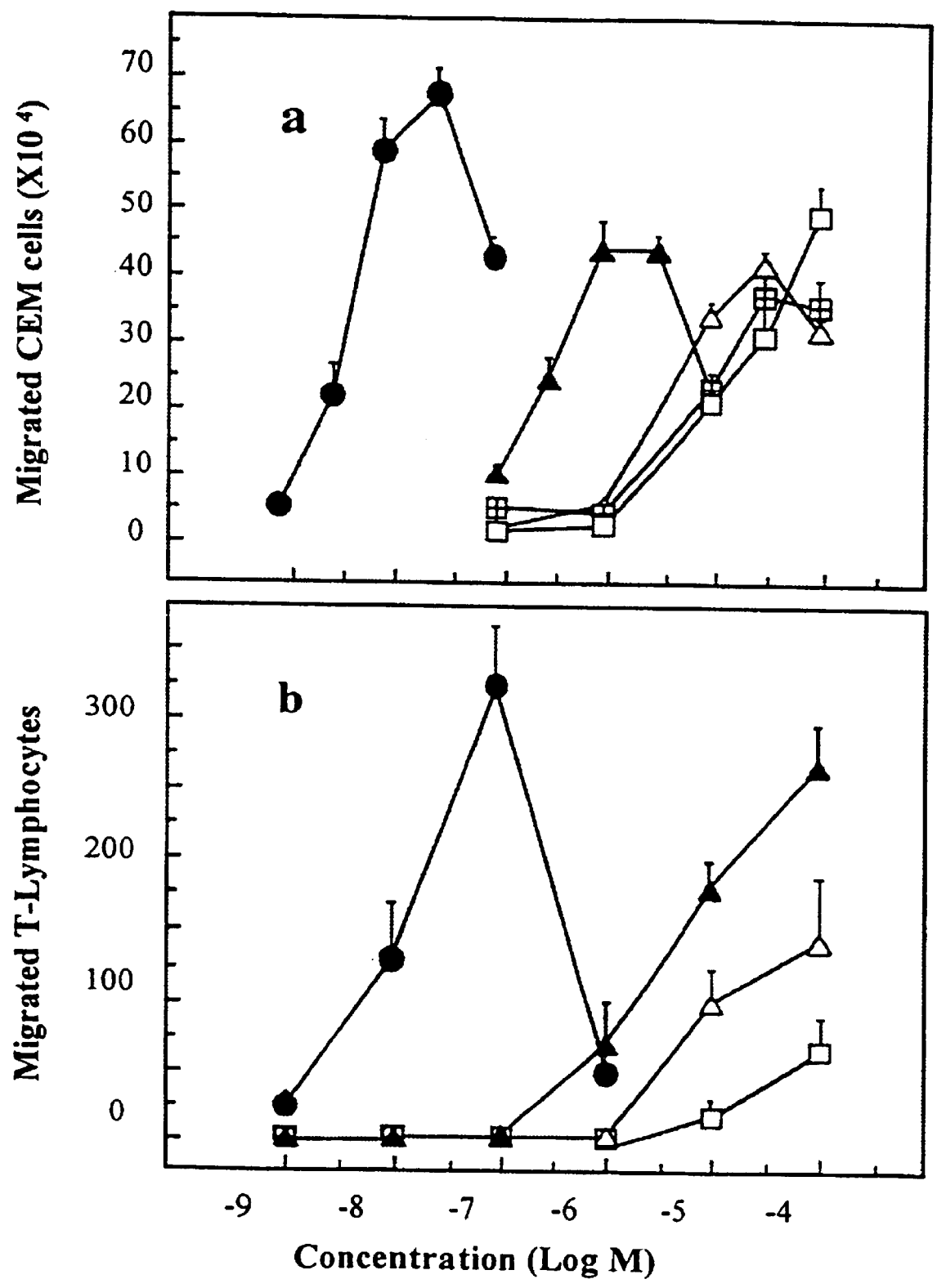
FIG. 2: Chemoattractant activity of SDF-1 peptides. Concentration dependent migration of CEM cells (a); and T-lymphocytes (b) in response to the SDF-1 peptides: 1–8 (□); 1λ (Δ); 1–9 dimer (▲); and 1–9[Aba] (⊞); and in response to native SDF-1 (●). The data shown are the means ± SD of migrated cells. Similar results were obtained in two additional experiments.

In one aspect, the invention provides a variety of therapeutic uses for CXCR4 antagonists. In various embodiments, CXCR4 antagonists may be used as therapeutically as follows, or to manufacture a medicament for such therapeutic treatments; reducing interferon gamma production by T-cells, treatment of an autoimmune disease, treatment of multiple sclerosis, treatment of other neurological diseases, treatment of cancer, and regulation of angiogenesis. In some aspects of the invention, CXCR4 inhibitors may be used, particularly in the treatment of multiple sclerosis, with or without beta interferon. The invention provides corresponding methods of medical treatment, in which a therapeutic dose of a CXCR4 antagonist is administered in a pharmacologically acceptable formulation. Accordingly, the invention also provides therapeutic compositions comprising a CXCR4 antagonist and a pharmacologically acceptable excipient or carrier, as described above. The therapeutic composition may advantageously be soluble in an aqueous solution at a physiologically acceptable pH.

In alternative embodiments, the CXCR4 antagonists for use in the invention may be peptide compounds comprising a substantially purified peptide fragment, modified fragment, analog or pharmacologically acceptable salt of SDF-1. In some embodiments, the peptide compound may comprise an N-terminal amino acid sequence KGVSLSYRC-$R_1$ (SEQ ID NO:2) wherein $R_1$ is selected from the group consisting of hydrogen and polypeptides homologous to at least a portion of SDF-1.

In a further embodiment, the peptide compound may comprise a dimerized N-terminal amino acid sequence. For example, an SDF-1(1–8)$_2$ dimer may be used, as represented here with the second polypeptide segment of the dimer written from the carboxyl to the amino end: KGVSLSYR-X-RYSLSVGK (a dimer of SEQ ID NO:3, as shown in FIG. 14). In another embodiment, the peptide compound may further comprise a dimerized N-terminal amino acid SDF-1)1–9)$_2$, represented here with the second dimer written from the carboxyl to the amino end): KGVSLSYRC-X-CRYSLSVGK, (a dimer of SEQ ID NO:4, as shown in FIG. 14). In such dimers, X may be a lysine amino acid wherein both the α- and ε-amino groups are associated with amide bond formulation and the lysyl carboxyl group may be protected. Similarly, X may be other moieties in which two amino groups are used to form a linkage between the peptides, such as ornithine or L-amino-N-butyric acid. The linkage may be between terminal carboxyl groups. In an alternative embodiment, X may be a benzene ring in which the peptides are attached at adjoining carbons on the ring. Alternatively, X may be any bridge-forming moiety that covalently links peptides so that a plurality of peptides are joined by the bridge to provide a plurality of N-terminals in the compounds.

DETAILED DESCRIPTION OF THE INVENTION

In accordance with various aspects of the invention, CXCR4 antagonists may be used to treat, or produce medicaments to treat, a variety of autoimmune disease. Such disease include multiple sclerosis, Guillain-Barre syndrome (GBS), Amyotrophic lateral sclerosis (ALS), and other diseases of nerves, rheumatoid arthritis, psoriasis, diabetes type I, ulcerative colitus, gout, lupus, and transplant rejections.

In accordance with one aspect of the invention, antagonists of CXCR4 may be used therapeutically to regulate angiogenesis and cell growth in human pathological diseases including cancers such as lymphoma and carcinoma, as well as restonosis. In one embodiment, as exemplified herein, two peptide CXCR4 antagonists have been used to inhibit angiogenesis and tumor growth in mouse models of mammalian cancers.

The SDF-1 antagonists of the invention may be used to inhibit gamma interferon production by activated T-cells. This may have particular application in the treatment of autoimmune disease, in which production of gamma interferon by T-cells is an art recognised disease marker. Examples of diseases which are known to be mediated by interferon gamma are MS (Proc. Natl. Acad Sci. Vol. 95; 675–680; 1998), Guillian-barre (Ann Neutol, Vol. 27; S57–S63; 1990), Autoimmune Kidney damage (J. Immunol, 161; 494–503, 1998), arthritis (Immunol, 95; 480–487; 1998) and various other neurological diseases (Acta. Neurol. Scad. 90; 19–25; 1994). More general descriptions of interferon gamma mediated autoimmune diseases can be found in J. Immunol. 161; 6878–6884; 1998 and J. Exp. Med. 186; 385–391; 1997. In one embodiment of the invention, the peptide antagonist SDF-1 (1–67) [P2G] has, for example, been used to inhibit production of gamma interferon by T-cells. Also, the peptide SDF-1 (1–9) P2G reduced gamma interferon release from human T-cells (ie. these peptides are regulators of human autoimmune diseases).

The invention also provides an assay to identify CXCR4 inhibitors that may be used to inhibit gamma interferon production, particularly in autoimmune disease. An embodiment of such an assay is disclosed in Example 2 herein.

In one embodiment, the assay comprises concanavalin A stimulated T-cells which release interferon gamma. In the assay, the T-cells are contacted with the putative CXCR4 antagonist and the degree of interferon gamma release is measured. The compounds to be assayed for antagonistic activity may be selected for their ability to decrease the amount of interferon gamma production.

Also within the scope of the present invention is an assay for compounds that inhibit angiogenesis. In the assay, a vascularized tumor in a mouse is contacted with the putative CXCR4 antagonist and the degree of vascularization is measured. The compounds to be assayed for anti-angiogenesis activity may be selected for their ability to decrease the amount of vascularization in a tumor.

In various aspects, the present invention utilizes CXCR4 antagonists. In some embodiments, the CXCR4 antagonists for use in the invention may be substantially purified peptide fragments, modified peptide fragments, analogues or pharmacologically acceptable salts of either SDF-1α or SDF-1β. SDF-1 derived peptide antagonists of CXCR4 may be identified by known physiological assays and a variety of synthetic techniques (such as disclosed in Crump et al., 1997, The EMBO Journal 16(23) 6996–7007; and Heveker et al., 1998, Current Biology 8(7): 369–376; each of which are incorporated herein by reference). Such analog of SDF-1 include homologs of native SDF-1, such as naturally occurring isoforms or genetic variants, or polypeptides having substantial sequence similarity to SDF-1, such as 40% sequence identity, 60% sequence identity or preferably 80% sequence identity to at least a portion of the native SDF-1 sequence, provided they have CXCR4 antagonistic activity. In some embodiments, chemically similar amino acids may be substituted for amino acids in the native SDF-1 sequence (to provide conservative amino acid substitutions). In some embodiments, peptides having an N-terminal LSY sequence motif within 10, or preferably within 7, amino acids of the N-terminus, and/or an N-terminal RFFESH (SEQ ID NO:5) sequence motif within 20 amino acids of the N-terminus may be used provided they have CXCR4 antagonistic activity. The single letter amino acid code and the three letter amino acid code are used interchangeably herein. One family of such peptide antagonist candidates has a KP motif as an N-terminal and an LSY motif at amino acids 5–7. Alternative peptides further include the RFFESH (SEQ ID NO: 5) motif at amino acids 12–17. In alternative embodiments, the LSY motif is located at positions 3–5 of a peptide. The invention also provides peptide dimers having two amino acids sequences, which may each have the foregoing sequence elements, attached by a disulfide bridge within 20, or preferably within 10, amino acids of the N terminus, linking cysteine residues or α-aminobutric acid residues.

Figure 3:
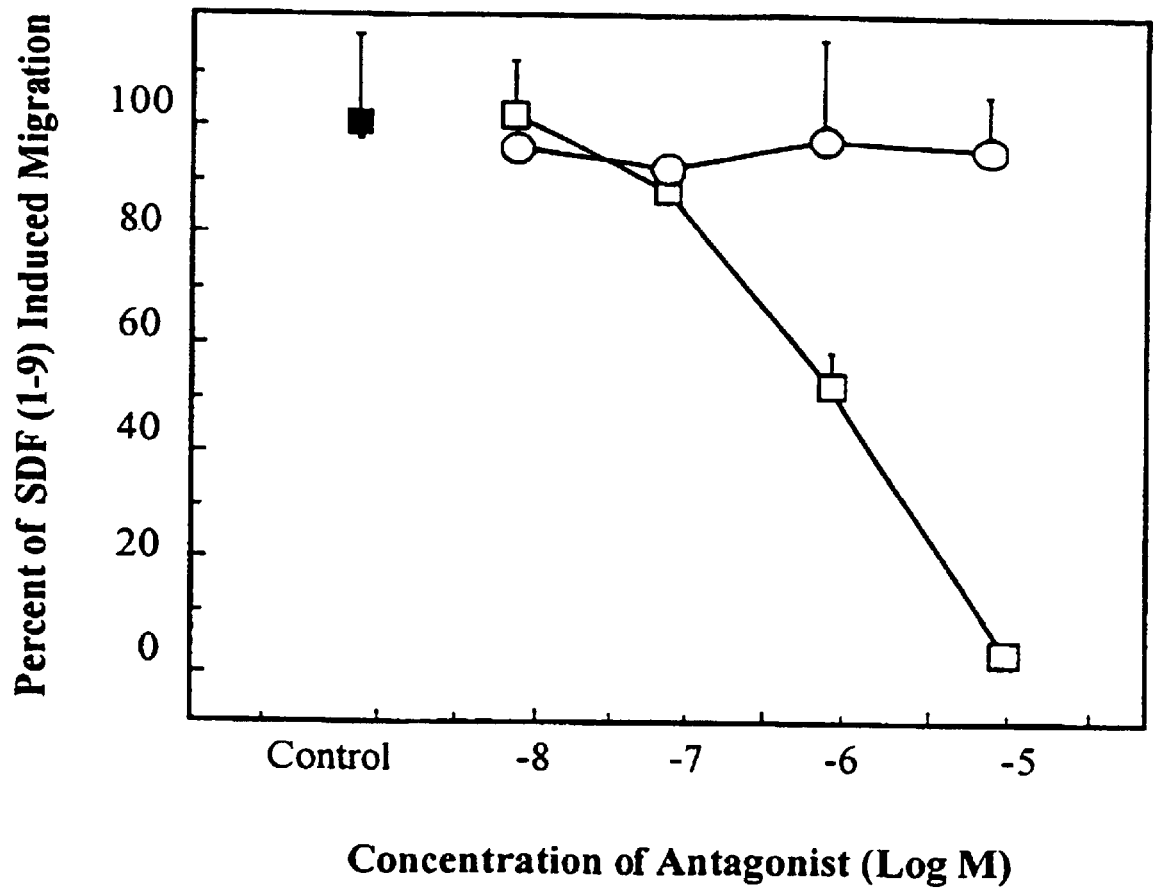
FIG. 3: Chemotaxis inhibition by chemokine antagonists. CEM cell migration induced by SDF-1 (1–9) peptide (10 μm) in the presence of the indicated concentrations of the SDF-1 antagonists. SDF-1 (1–67) [P2G] (◉); or the IL-8 antagonist, IL-8 (6–72) (•). Migrations is expressed as percent of the response obtained in the absence of antagonist (control, ■). The data shown are the means ± SD of duplicate determination from two separate experiments.
Figure 4:
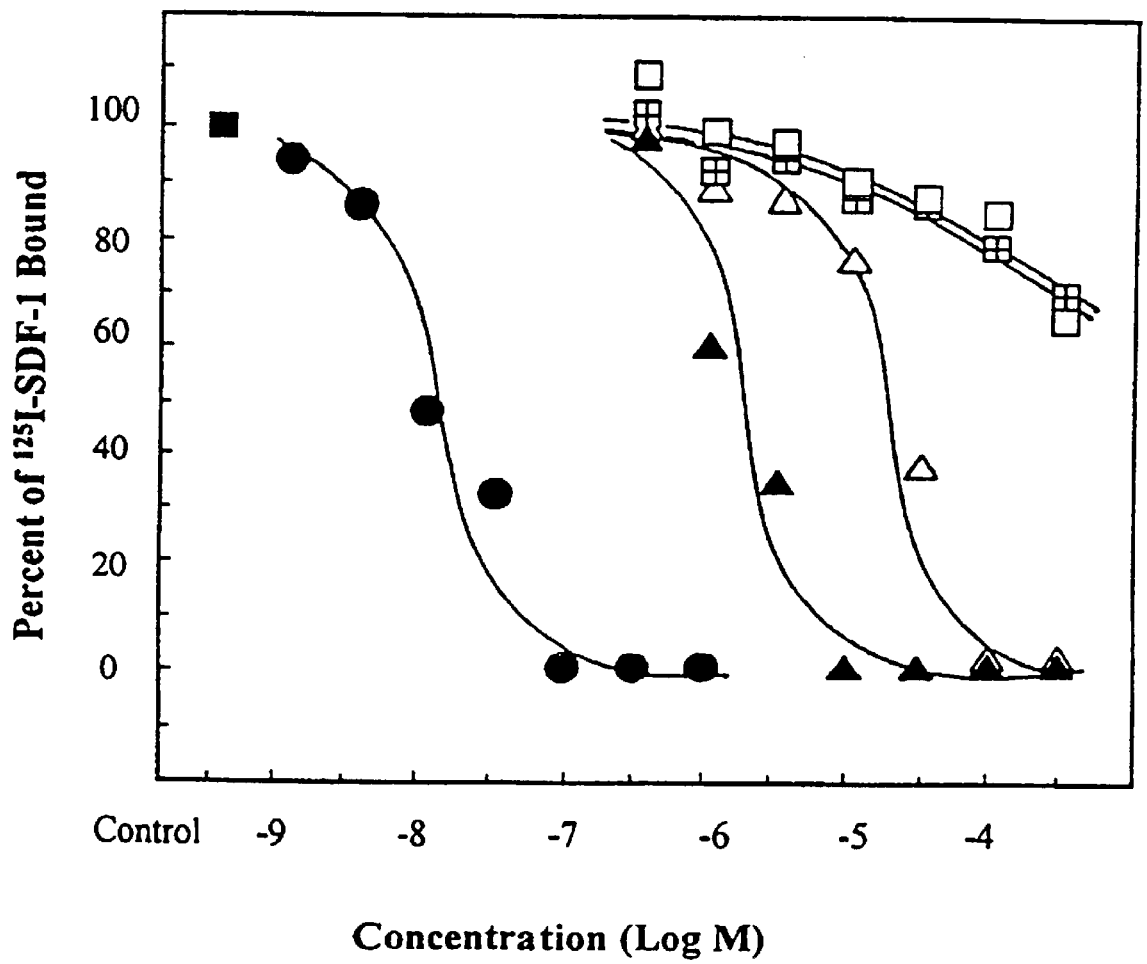
FIG. 4: Receptor binding of SDF-1 peptides. Competition for specific binding of $^{125}$I-SDF-1 (4 nM) to CEM cells by 1–8 (□); 1–9 (Δ); 1–9 dimer (▲); 1–9[Aba-9] (⊞; native SDF-1 (●). The percentage specific cpm bound in the absence of competitor (◳); is shown. Representative results from two to six experiments.

In one aspect, the invention provides CXCR4 antagonists in which glycine is substituted for proline at amino acid position 2. The full (67 amino acid long) versions of this analog, designated SDF-1(1–67) [P2G], is a potent CXCR4 receptor antagonist (Crump et al., 1997, The EMBO Journal 16 (23) 6996–2007. A variety of small SDF-1 peptide analogues may also be used as CXCR4 antagonists. One such peptide is a dimer of amino acids 1–9, with glycine substituted for proline in each member of the dimer at position 2, in which the amino acid chains are joined by a disulphide bond between each of the cysteines at position 9 in each sequence (designated SDF-1 (1–9[P2G]($_2$). SDF-1 (1–9[P2G])$_2$ lacked detectable chemotaxic activity (FIG. 2$a$), but it competed for SDF-1 binding with similar affinity to a SDF-1 (1–9)$_2$ dimer (FIG. 4). The SDF-1 (1–9[P2G])$_2$ dimer inhibited SDF-1 activity in a dose dependent manner (FIG. 3$b$). 50 μM of SDF-1 (1–9[P2G])$_2$ dimer was required to inhibit the activity of 10 nM of SDF-1 by 50 % a ratio of 5,000.

The invention provides pharmaceutical compositions containing CXCR4 antagonists. In one embodiment, such compositions include a CXCR4 antagonist compound in a therapeutically or prophylactically effective amount sufficient to alter, and preferably inhibit, production of gamma interferon, and a pharmaceutically acceptable carrier. In another embodiment, the composition includes a CXCR4 antagonist compound in a therapeutically or prophylactically effective amount sufficient to inhibit the angiogenesis, preferably angiogenesis associated with carcinomas and lymphomas, and a pharmaceutically acceptable carrier. A "therapeutically effective amount" refers to an amount effective, at dosages and for periods of time necessary, to achieve the desired therapeutic result, such as reduction or reversal of angiogenesis in the case of cancers, or reduction or inhibition of gamma interferon production from T-cells in the case of autoimmune diseases. A therapeutically effective amount of CXCR4 antagonist may vary according to factors such as the disease state, age, sex, and weight of the individual, and the ability of the CXCR4 antagonist to elicit a desired response in the individual. Dosage regimens may be adjusted to provide the optimum therapeutic response. A therapeutically effective amount is also one in which any toxic or detrimental effects of the CXCR4 antagonist are outweighed by the therapeutically beneficial effects. A "prophylactically effective amount" refers to an amount effective, at dosages and for periods of time necessary, to achieve the desired prophylactic result, such as preventing or inhibiting the rate of metastasis of a tumour or the onset of bouts or episodes of multiple sclerosis. A prophylactically effective amount can be determined as described above for the therapeutically effective amount. Typically, since a prophylactic dose is used in subjects prior to or at an earlier stage of disease, the prophylactically effective amount will be less than the therapeutically effective amount.

In particular embodiments, a preferred range for therapeutically or prophylactically effective amounts of CXCR4 antagonist may be 0.1 nM–0.1 M, particularly 0.1 nM–0.05 M, more particularly 0.05 nM–15 μM and most particularly 0.01 nM–10 μM. It is to be noted that dosage values may vary with the severity of the condition to be alleviated, especially with multiple sclerosis. It is to be further understood that for any particular subject, specific dosage regimens should be adjusted over time according to the individual need and the professional judgement of the person administering or supervising the administration of the compositions, and that dosage ranges set forth herein are exemplary only and are not intended to limit the scope or practice of the claimed composition.

The amount of active compound in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

As used herein "pharmaceutically acceptable carrier" or "exipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as manifold, sorbitol, or sodium chloride in the composition. Prolonged absorption of the injectable compositions can be brought about by including in the composition an agent which delays absorption, for example, monostearate salts and gelatin. Moreover, the CXCR4 antagonists can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound (e.g. CXCR4 antagonist) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In accordance with an alternative aspect of the invention, a CXCR4 antagonist may be formulated with one or more additional compounds that enhance the solubility of the CXCR4 antagonist.

Another aspect of the invention pertains to a method for selecting CXCR4 antagonists which bind to the CXCR4 receptor. In the method, a test compound is contacted with activated human T-cells, the production of gamma interferon is measured and a CXCR4 antagonist is selected based on the ability of the test compound to decrease or inhibit the production of gamma interferon. The test compound may be a substantially purified peptide fragment, modified fragment, analog or pharmacologically acceptable salt of either SDF-1α or SDF-1β. In a preferred embodiment, the test compound is contacted with a molar excess amount of the T-cells. The amount and/or rate of gamma interferon production in the presence of the test compound can be determined by a suitable assay, as described elsewhere herein. In the presence of a test compound that inhibits gamma interferon production, the production of gamma interferon is reduced compared to when the CXCR4 antagonist is absent.

CXCR4 antagonist compounds of the invention include SDF-1 derivatives, such as C-terminal hydroxymethyl derivatives, O-modified derivatives (e.g., C-terminal hydroxymethyl benzyl ether), N-terminally modified derivatives including substituted amides such as alkylamides and hydrazides and compounds in which a C-terminal phenylalanine residue is replaced with a phenethylamide analogue (e.g., Ser-Ile-phenethylamide as an analogue of the tripeptide Ser-Ile-Phe).

Within a CXCR4 antagonist compound of the invention, a peptidic structure (such as an SDF-1 derived peptide) maybe coupled directly or indirectly to at least one modifying group. The term "modifying group" is intended to include structures that are directly attached to the peptidic structure (e.g., by covalent coupling), as well as those that are indirectly attached to the peptidic structure (e.g., by a stable non-covalent association or by covalent coupling to additional amino acid residues, or mimetics, analogues or derivatives thereof, which may flank the SDF-1 core peptidic structure). For example, the modifying group can be coupled to the amino-terminus or carboxy-terminus of an SDF-1 peptidic structure, or to a peptidic or peptidomimetic region flanking the core domain. Alternatively, the modifying group can be coupled to a side chain of at least one amino acid residue of a SDF-1 peptidic structure, or to a peptidic or peptido-mimetic region flanking the core domain (e.g., through the epsilon amino group of a lysyl residue(s), through the carboxyl group of an aspartic acid residue(s) or a glutamic acid residue(s), through a hydroxy group of a tyrosyl residue(s), a serine residue(s) or a threonine residue(s) or other suitable reactive group on an amino acid side chain). Modifying groups covalently coupled to the peptidic structure can be attached by means and using methods well known in the art for linking chemical structures, including, for example, amide, alkylamino, carbamate or urea bonds.

The term "modifying group" is intended to include groups that are not naturally coupled to natural SDF-1 peptides in their native form. Accordingly, the term "modifying group" is not intended to include hydrogen. The modifying group(s) is selected such that the CXCR4 antagonist compound alters, and preferably inhibits, gamma interferon production.

The invention also provides "modifying groups" selected such that the CXCR4 antagonist compound inhibits angiogenesis of tumours when contacted with the T-cells or the tumour respectively.

In a preferred embodiment, the modifying group(s) comprises a cyclic, heterocyclic or polycyclic group. The term "cyclic group", as used herein, is intended to include cyclic saturated or unsaturated (i.e., aromatic) group having from about 3 to 10, preferably about 4 to 8, and more preferably about 5 to 7, carbon atoms. Exemplary cyclic groups include cyclopropyl, cyclobutyl, cyclopentyl, cyclohexyl, and cyclooctyl. Cyclic groups may be unsubstituted or substituted at one or more ring positions. Thus, a cyclic group may be substituted with, e.g., halogens, alkyls, cycloalkyls, alkenyls, alkynyls, aryls, heterocycles, hydroxyls, aminos, nitros, thiols amines, imines, amides, phosphonates, phosphines, carbonyls, carboxyls, silyls, ethers, thioethers, sulfonyls, sulfonates, selenoethers, ketone, aldehydes, esters, —$CF_3$, —CN, or the like.

The term "heterocyclic group" is intended to include cyclic saturated or unsaturated (i.e., aromatic) group having from about 3 to 10, preferably about 4 to 8, and more preferably about 5 to 7, carbon atoms, wherein the ring structure includes about one to four heteroatoms. Heterocyclic groups include pyrrolidine, oxolane, thiolane, imidazole, oxazole, piperidine, piperazine, morpholine. The heterocyclic ring can be substituted at one or more positions with such substituents as, for example, halogens, alkyls, cycloalkyls, alkenyls, alkynyls, aryls, other heterocycles, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —$CF_3$, —CN, or the like. Heterocycles may also be bridged or fused to other cyclic groups as described below.

The term "polycyclic group" as used herein is intended to refer to two or more saturated or unsaturated (i.e., aromatic) cyclic rings in which two or more carbons are common to two adjoining rings, eg., the rings are "fused rings". Rings that are joined through non-adjacent atoms are termed "bridged" rings. Each of the rings of the polycyclic group can be substituted with such substituents as described above, as for example, halogens, alkyls, cycloalkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —$CF_3$, —CN, or the like.

The term "alkyl" refers to the radical of saturated aliphatic groups, including straight chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 20 or fewer carbon atoms in its backbone (e.g., $C_1$-$C_{20}$ for straight chain, $C_3$-$C_{20}$ for branched chain), and more preferably 10 or fewer. Likewise, preferred cycloalkyls have from 4–10 carbon atoms in their ring structure, and more preferably have 5, 6 or 7carbons in the ring structure. Unless the number of carbons is otherwise specified, "lower alkyl" as used herein means an alkyl group, as defined above, but having from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, carbonyl (such as carboxyl, ketones (including alkylcarbonyl and arylcarbonyl groups), and esters (including alkyloxycarbonyl and aryloxycarbonyl groups)), thiocarbonyl, acyloxy, alkoxyl, phosphoryl, phosphonate, phosphinate, amino, acylamino, amido, amidine, imino, cyano, nitro, azido, sulfhydryl, alkylthio, sulfate, sulfonate, sulfamoyl, sulfonamido, heterocyclyl, aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of aminos, azidos, iminos, amidos, phosphoryls (including phosphonates and phosphinates), sulfonyls (including sulfates, sulfonamidos, sulfamoyls, and sulfonates), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The terms "alkenyl" and "alkynyl" refer to unsaturated aliphatic groups analogous in length and possible substitution to the alkyls described above, but that contain at least one double or triple bond respectively.

The term "aralkyl", as used herein, refers to an alkyl or alkylenyl group substituted with at least one aryl group (e.g., an aromatic or heteroaromatic group). Exemplary aralkyls include benzyl (i.e., phenylmethyl), 2-naphthylethyl, 2-(2-pyridyl)propyl, 5-dibenzosuberyl, and the like.

The term "alkylcarbonyl", as used herein, refers to —C(O)-alkyl. Similarly, the term "arylcarbonyl" refers to —C(O)-aryl. The term "alkoxycarbonyl", as used herein, refers to the group —C(O)—O-alkyl, and the term "aryloxycarbonyl" refers to —C(O)—O-aryl. The term "acyloxy" refers to —O—C(O)—$R_7$, in which $R_7$ is alkyl, alkenyl, alkynyl, aryl, aralkyl or heterocyclyl.

The term "amino", as used herein, refers to —$N(R_8)$ ($R_9$), in which $R_8$ and $R_9$ are each independently hydrogen, alkyl, alkyenyl, alkynyl, aralkyl, aryl and $R_8$ and $R_9$, together with the nitrogen atom to which they are attached, form a ring having 4–8 atoms. Thus, the term "amino", as used herein, includes unsubstituted, monosubstituted (e.g., monoalkylamino or monoarylamino), and disubstituted (e.g., dialkylamino or alkylarylamino) amino groups. The term "amido" refers to —C(O)—N($R_8$)($R_9$), in which $R_8$ and $R_9$ are as defined above. The term "acylamino" refers to —N(R'$_8$)C(O)—$R_7$, in which $R_7$ is as defined above and R'$_8$ is alkyl.

As used herein, the term "nitro" means —$NO_2$; there term "halogen" designates —F, —Cl, —Br or —I; the term "sulfhydryl" means —SH; and the term "hydroxyl" means —OH.

The term "aryl" as used herein includes 5-, 6- and 7-membered aromatic groups that may include from zero to four heteroatoms in the ring, for example, phenyl, pyrrolyl, furyl, thiophenyl, imidazolyl, oxazole, thiazolyl, triazolyl, pyrazolyl, pyridyl, pyrazinyl, pyridazinyl and pyrimidinyl, and the like. Those aryl groups having heteroatoms in the ring structure may also be referred to as "aryl heterocycles" or "heteroatomatics". The aromatic ring can be substituted at one or more ring positions with such substituents as described above, as for example, halogen, azide, alkyl, aralkyl, alkenyl, alkynyl, cycloalkyl, hydroxyl, amino, nitro, sulfhydryl imino, amido, phosphonate, phosphinate, carbonyl, carboxyl, silyl, ether, alkylthio, sulfonyl, sulfonyl, sulfonamido, ketone, aldehyde, ester, a heterocycle, an aromatic or heteroaromatic moiety, —$CF_3$, —CN, or the like. Aryl groups can also be part of a polycyclic group. For example, aryl groups include fused atomatic moieties such as naphthyl, anthracenyl, quinolyl, indolyl, and the like.

A CXCR4 antagonist compound can be modified at its carboxy terminus with a cholyl group according to methods known in the art (see e.g., Wess, G. et al. (1993) Tetrahedron Letters, 34:817–822; Wess, G. et al. (1992) Tetrahedron Letters 33:195–198; and Kramer, W. et al. (1992) J. Biol. Chem. 267:18598–18604). Cholyl derivatives and analogues can also be used as modifying groups. For example, a preferred cholyl derivative is Aic (3-(O-aminoethyl-iso)-cholyl), which has a free amino group that can be used to further modify the CXCR4 antagonist compound.

In one embodiment, the modifying group may be a "biotinyl structure", which includes biotinyl groups and analogues and derivatives thereof (such as a 2-iminobiotinyl group). In another embodiment, the modifying group can comprise a "fluorescein-containing group", such as a group derived from reacting an SDF-2 derived peptidic structure with 5- (and 6-)-carboxyfluorescein, succinimidyl ester or fluorescein isothiocyanate. In various other embodiments, the modifying group(s) can comprise an N-acetylneuraminyl group, a trans-4-cotininecarboxyl group, a 2-imino-1-imidazolidineacetyl group, an (S)-(−)-indoline-2-carboxyl group, a (−)-menthoxyacetyl group, a 2-norbornaneacetyl group, a γ-oxo-5-acenaphthenbutyryl, a (−)-2-oxo-4-thiazolidinecarboxyl group, a tetrahydro-3-furoyl group, a 2-iminobiotinyl group, a diethylenetriaminepentaacetyl group, a 4-morpholinecarbonyl group, a 2-thiopheneacetyl group or a 2-thiophenesulfonyl group.

Modifying groups may include groups comprising biotinyl structures, fluorescein-containing groups, a diethylenetriaminepentaacetyl group, a (−)-menthoxyacetyl group, and a N-acetylneuraminyl group. More preferred modifying groups those comprising a cholyl structure or an iminobiotinyl group.

In addition the cyclic, heterocyclic and polycyclic groups discussed above, other types of modifying groups can be used in a CXCR4 antagonist of the invention. For example, small hydrophobic groups may be suitable modifying groups. An example of a suitable non-cyclic modifying group is an acetyl group.

A CXCR4 antagonist compound of the invention can be further modified to alter the specific properties of the compound while retaining the ability of the compound to either inhibit angiogenesis or inhibit gamma interferon production. For example, in one embodiment, the compound is further modified to alter a pharmacokinetic property of the compound, such as in vivo stability or half-life. In another embodiment, the compound is further modified to label the compound with a detectable substance. In yet another embodiment, the compound is further modified to couple the compound to an additional therapeutic moiety.

To further chemically modify the compound, such as to alter its pharmacokinetic properties, reactive groups can be derivatized. For example, when the modifying group is attached to the amino-terminal end of the SDF-1 core domain, the carboxy-terminal end of the compound can be further modified. Preferred C-terminal modifications include those which reduce the ability of the compound to act as a substrate for carboxypeptidases. Examples of preferred C-terminal modifiers include an amide group, an ethylamide group and various non-natural amino acids, such as D-amino acids and β-alanine. Alternatively, when the modifying group is attached to the carboxy-terminal end of the aggregation core domain, the amino-terminal end of the compound can be further modified, for example, to reduce the ability of the compound to act as a substrate for aminopeptidases.

A CXCR4 antagonist compound can be further modified to label the compound by reacting the compound with a detectable substance. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{14}C$, $^{123}I$, $^{124}I$, $^{125}I$, $^{131}I$, $^{99m}Tc$, $^{35}S$ or $^{3}H$. In a preferred embodiment, a CXCR4 antagonist compound is radioactively labeled with $^{14}C$, either by incorporation of $^{14}C$ into the modifying group or one or more amino acid structures in the CXCR4 antagonist compound. Labeled CXCR4 antagonist compounds can be used to assess the in vivo pharmacokinetics of the compounds, as well as to detect disease progression or propensity of a subject to develop a disease, for example for diagnostic purposes. Tissue distribution CXCR4 receptors can be detected using a labeled CXCR4 antagonist compound either in vivo or in an in vitro sample derived from a subject.

For use as an in vivo diagnostic agent, a CXCR4 antagonist compound of the invention may be labeled with radioactive technetium or iodine. A modifying group can be chosen that provides a site at which a chelatin group for the label can be introduced, such as the Aic derivative of cholic acid, which has a free amino group. In another embodiment, the invention provides a CXCR4 antagonist compound labeled with radioactive iodine. For example, a phenylalanine residue within the SDF-1 sequence (such as amino acid residue 13) can be substituted with radioactive iodotyrosyl. Any of the various isotopes of radioactive iodine can be incorporated to create a diagnostic agent. Preferably, $^{123}I$ (half-life=13.2 hours) is used for whole body scintigraphy, $^{124}I$ (half life=4 days) is used for position emission tomography (PET), $^{125}I$ (half life=60 days) is used for metabolic turnover studies and $^{131}I$ (half life=8 days) is used for whole body counting and delayed low resolution imaging studies.

An additional modification of a CXCR4 antagonist compound of the invention may serve to confer an additional therapeutic property on the compound. That is, the additional chemical modification can comprise an additional functional moiety. For example, a functional moiety which serves to cause apoptosis of tumour cells, can be coupled to the CXCR4 antagonist compound. In this form, the SDF-1 derived portion of the CXCR4 antagonist may serve to target the compound to the tumour and inhibit angiogenesis, whereas the additional functional moiety serves to cause apoptosis of the cancerous cells after the compound has been targeted to these sites.

In an alternative chemical modification, a compound of the inventive is prepared in a "prodrug" form, wherein the compound itself does not modulate gamma interferon production or angiogenesis of a tumour, but rather is capable of being transformed, upon metabolism in vivo, into a CXCR4 antagonist compound as defined herein. For example, in this type of compound, the modulating group can be present in a prodrug form that is capable of being converted upon metabolism into the form of an active CXCR4 antagonist. Such a prodrug form of a modifying group is referred to herein as a "secondary modifying group." A variety of strategies are known in the art for preparing peptide prodrugs that limit metabolism in order to optimize delivery of the active form of the peptide-based drug (see e.g., Moss, J. (1995) in Peptide-Based Drug Design: Controlling Transport and Metabolism, Taylor, M. D. and Amidon, G. L. (eds), Chapter 18.

CXCR4 antagonist compounds of the invention can be prepared by standard techniques known in the art. The peptide component of a CXCR4 antagonist is composed, at least in part, of a peptide, which can be synthesized using standard techniques such as those described in Bodansky, M. Principles of Peptide Synthesis, Springer Verlag, Berlin (1993) and Grant, G. A. (ed.). Synthetic Peptides: A User's Guide, W. H. Freeman and Company, New York (1992). Automated peptide synthesizers are commercially available (e.g., Advanced ChemTech Model 396, Milligen/Biosearch 9600). Additionally, one or more modulating groups can be attached to the SDF-1 derived peptidic component by standard methods, for example using methods for reaction through an amino group (e.g., the alpha-amino group at the amino-terminus of a peptide), a carboxyl group (e.g., at the carboxy terminus of a peptide), a hydroxyl group (e.g., on a tyrosine, serine or threonine residue) or other suitable reactive group on an amino acid side chain (see e.g., Greene, T. W. and Wuts, P. G. M. Protective Groups in Organic Synthesis, John Wiley and Sons, Inc., New York (1991)). Exemplary synthesis of preferred CXCR4 antagonists is described further in the Examples.

Peptides of the invention may be chemically synthesized using standard techniques such as those described in Bodansky, M. Principles of Peptide Synthesis, Springer Verlag, Berlin (1993) and Grant, G. A. (ed.). Synthetic Peptides: A User's Guide, W. H. Freeman and Company, New York (1992) (all of which are incorporated herein by reference). Automated peptide synthesizers as commercially available (e.g., Advanced ChemTech Model 396; Milligen/Biosearch 9600).

In another aspect of the invention, peptides may be prepared according to standard recombinant DNA techniques using a nucleic acid molecule encoding the peptide. A nucleotide sequence encoding the peptide can be determined using the genetic code and oligonucleotide molecule having this nucleotide sequence can be synthesized by standard DNA synthesis methods (e.g., using an automated DNA synthesizer). Alternatively, a DNA molecule encoding a peptide compound can be derived from the natural precursor protein gene or cDNA (e.g., using the polymerase chain reaction (PCR) and/or restriction enzyme digestion) according to standard molecular biology techniques.

The invention also provides an isolated nucleic acid molecule comprising a nucleotide sequence encoding a peptide of the invention. In some embodiments, the peptide may comprise an amino acid sequence having at least one amino acid deletion compared to native SDF-1. As used herein, the term "nucleic acid molecule" is intended to include DNA molecules and RNA molecules and may be single-stranded or double-stranded. In alternative embodiments, the isolated nucleic acid encodes a peptide wherein one or more amino acids are deleted from the N-terminus, C-terminus and/or an internal site of SDF-1. In yet other embodiments, the isolated nucleic acid encodes a peptide fragment having one or more amino acids deleted compared to native SDF-1.

To facilitate expression of a peptide compound in a host cell by standard recombinant DNA techniques, the isolated nucleic acid encoding the peptide may be incorporated into a recombinant expression vector. Accordingly, the invention also provides recombinant expression vectors comprising the nucleic acid molecules of the invention. As used herein, the term "vector" refers to a nucleic acid molecule capable of transporting another nucleic acid to which it has been linked. One type of vector is a plasmid, which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors".

In recombinant expression vectors of the invention, the nucleotide sequence encoding a peptide may be operatively linked to one or more regulatory sequences, selected on the basis of the host cells to be used for expression. The terms "operatively linked" or "operably" linked mean that the sequences encoding the peptide are linked to the regulatory sequence(s) in a manner that allows for expression of the peptide compound. The term "regulator sequence" includes promoters, enhancers, polyadenylation signals and other expression control elements. Such regulatory sequences are described, for example, in Goeddel; Gene Expression Technology; Methods and Enzymology 185, Academic Press, San Diego, Calif. (1990) (incorporated herein be reference). Regulatory sequences include those that direct constitutive expression of a nucleotide sequence in many types of host cell, those that direct expression of the nucleotide sequence only in certain host cells (e.g., tissue-specific regulatory sequences) and those that direct expression in a regulatable manner (e.g., only in the presence of an inducing agent). It will be appreciated by those skilled in the art that the design of the expression vector may depend on such factors as the choice of the host cell to be transformed, the level of expression of peptide compound desired, etc. The expression vectors of the invention can be introduced into host cells thereby to produce peptide compounds encoded by nucleic acids as described herein.

The recombinant expression vectors of the invention can be designed for expression of peptide compounds in prokaryotic or eukaryotic cells. For example, peptide compounds can be expressed in bacterial cells such as E. coli, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector may be transcribed and translated in vitro, for example using T7 promoter regulatory sequences and T7 polymerase. Examples of vectors for expression in yeast S. cerivisae include pYepSecl (Baldari et al., (1987) EMBO J. 6:229–234), pMFa (Kurjan and Herskowitz, (1982) Cell 30:933–943), pJRY88 (Schultz et al., (1987) Gene 54:113–123), and pYES2 (Invitrogen Corporation, San Diego, Calif.). Baculovirus vectors available for expression of proteins or peptides in cultured insect cells (e.g., Sf 9 cells) include the pAc series (Smith et al., (1983) Mol. Cell. Biol. 3:2156–2165) and the pVL series (Lucklow, V. A., and Summers, M. D., (1989) Virology 170:31–39). Examples of mammalian expression vectors include pCDM8 (Seed, B., 1987) Nature 329:840) and pMT2PC (Kaufman et al. (1987), EMBO J. 6:187–195). When used in mammalian cells, the expression vector's control functions are often provided by viral regulatory elements. For example, commonly used promoters are derived from polyoma, Adenovirus 2, cytomegalovirus and Simian Virus 40.

In addition to the regulatory control sequences discussed above, the recombinant expression vector may contain additional nucleotide sequences. For example, the recombinant expression vector may encode a selectable marker gene to identify host cells that have incorporated the vector. Such selectable marker genes are well known in the art. Moreover, the facilitate secretion of the peptide compound from a host cell, in particular mammalian host cells, the recombinant expression vector preferably encodes a signal sequence operatively linked to sequences encoding the amino-terminus of the peptide compound such that upon expression, the peptide compound is synthesised with the signal sequence fused to its amino terminus. This signal sequence directs the peptide compound into the secretory pathway of the cell and is then cleaved, allowing for releasing of the mature peptide compound (i.e., the peptide compound without the signal sequence) from the host cell. Use of a signal sequence to facilitate secretion of proteins or peptides from mammalian host cells is well known in the art.

A recombinant expression vector comprising a nucleic acid encoding a peptide compound that either inhibits gamma interferon production or inhibits angiogenesis can be introduced into a host cell to thereby produce the peptide compound in the host cell. Accordingly, the invention also provides host cells containing the recombinant expression vectors of the invention. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. A host cell may be any prokaryotic or eukaryotic cell. For example, a peptide compound may be expressed in bacterial cells such as E. coli, insect cells, yeast or mammalian cells. Preferably, the peptide compound is expressed in mammalian cells. In a preferred embodiment, the peptide compound is expressed in mammalian cells in vivo in a mammalian subject to treat oasis in the subject through gene therapy (discussed further below). Preferably, the peptide compound encoded by the recombinant expression vector is secreted from the host cell upon being expressed in the host cell.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, electroporation, microinjection and viral-mediated transfection. Suitable methods for transforming or transfecting host cells can be found in Sambrook et al. (Molecular Cloning: A Laboratory Manual, 2nd Edition, Cold Spring Harbor Laboratory press (1989)), and other laboratory manuals. Methods for introducing DNA into mammalian cells in vivo are also known in the art and can be used to deliver the vector DNA to a subject for gene therapy purposes (discussed further below).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the genes of interest. Preferred selectable markers include those that confer resistance to drugs, such as G418, hygromycin and methotrexate. Nucleic acid encoding a selectable marker may be introduced into a host cell on the same vector as that encoding the peptide compound or may be introduced on a separate vector. Cells stably transfected with the introduced nucleic acid can be identified by drug selection (e.g., cells that have incorporated the selectable marker gene will survive, while the other cells die).

A nucleic acid of the invention can be delivered to cells in vivo using methods known in the art, such as direct injection of DNA, receptor-mediated DNA uptake or viral-mediated transfection. Direct injection has been used to introduce naked DNA into cells in vivo (see e.g., Acsadi et al. (1991) Nature 332:815–818; Wolff et al. (1990) Science 247:1465–1468). A delivery apparatus (e.g., a "gene gun") for injecting DNA into cells in vivo can be used. Such an apparatus is commercially available (e.g., from BioRad). Naked DNA can also be introduced into cells by complexing the DNA to a cation, such as polylysine, which is coupled to a ligand for a cell-surface receptor (see for example Wu, G. and Wu, C. H. (1988) J. Biol. Chem. 263:14621; Wilson et al. (1992) J. Biol. Chem. 267:963–967; and U.S. Pat. No. 5,166,320). Binding of the DNA-ligand complex to the receptor facilitates uptake of the DNA by receptor-mediated endocytosis. Additionally, a DNA-ligand complex linked to adenovirus capsids which naturally disrupt endosomes, thereby releasing material into the cytoplasm can be used to avoid degradation of the complex by intracellular lysosomes (see for example Curiel et al. (1991) Proc. Natl. Acad. Sci. USA 88:8850; Cristiano et al. (1993) Proc. Natl. Acad. Sci. USA 90:2122–2126).

Defective retroviruses are well characterized for use in gene transfer for gene therapy purposes (for a review see Miller, A. D. (1990) Blood 76:271). Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines include .pψi.Crip, . pψi.Cre, .pψi.2 and .pψi.Am. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) Science 230:1395–1398; Danos and Mulligan (1988) Proc. Natl. Acad. Sci. USA 85:6460–6464; Wilson et al. (1988) Proc. Natl. Acad. Sci. USA 85:3014–3018; Armentano et al. (1990) Proc. Natl. Acad. Sci. USA 87:6141–6145; Huber et al. (1991) Proc. Natl. Acad. Sci. USA 88:8039–8043; Ferry et al. (1991) Proc. Natl. Acad. Sci. USA 88:8377–8381; Chowdhury et al. (1991) Science 254:1802–1805; van Beusechem et al. (1992) Proc. Natl. Acad. Sci. USA 89:7640–7644; Kay et al. (1992) Human Gene Therapy 3:641–647; Dai et al. (1992) Proc. Natl. Acad. Sci. USA 89:10892–10895; Hwu et al. (1993) J. Immunol. 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Alternatively, the genome of an adenovirus can be manipulated such that it encodes and expresses a peptide compound of the invention, but is inactivated in terms of its ability to replicate in a normal lytic viral life cycle. See for example Berkner et al. (1988) BioTechniques 6:616; Rosenfeld et al. (1991) Science 252:431–434; and Rosenfeld et al. (1992) Cell 68:143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) Proc. Natl. Acad. Sci. USA 89:6482–6486), hepatocytes (Herz and Gerard (1993) Proc. Natl. Acad. Sci. USA 90:2812–2816) and muscle cells (Quantin et al. (1992) Proc. Natl. Acad. Sci. USA 89:2581–2584).

Adeno-associated virus (AAV) can also be used for delivery of DNA for gene therapy purposes. AAV is a naturally occurring defective virus that requires another virus, such as an adenovirus or a herpes virus, as a helper virus for efficient replication and a productive life cycle. (For a review see Muzyczka et al. Curr. Topics in Micro. and Immunol. (1992) 158:97–129). It is also one of the few viruses that may integrate its DNA into non-dividing cells, and exhibits a high frequency of stable integration (see for example Flotte et al. (1992) Am. J. Respir. Cell. Mol. Biol. 7:349–356; Samulski et al. (1989) J. Virol. 63:3822–3828; and McLaughlin et al. (1989) J. Virol. 62:1963–1973). An AAV vector such as that described in Tratschin et al. (1985) Mol. Cell Biol. 5:3251–3260 can be used to introduce DNA into cells. A variety of nucleic acids have been introduced into different cell types using AAV vectors (see for example Hermonat et al. (1984) Proc. Natl. Acad. Sci. USA 81:6466–6470; Tratschin et al. (1985) Mol. Cell. Biol. 4:2072–2081; Wondisford et al. (1988) Mol. Endocrinol. 2:32–39; Tratschin et al. (1984) J. Virol. 51:611–619; and Flotte et al. (1993) J. Biol. Chem. 268:3781–3790).

In another embodiment, the invention provides a method for treating a subject suffering from cancer or an autoimmune disease (e.g. multiple sclerosis), comprising administering to the subject a recombinant expression vector encoding the SDF-1 derived peptide compound such that the peptide compound is synthesised in the subject and the subject is treated for a disorder associated with cancer or an autoimmune disease. The peptide compound may comprise a peptide fragment having at least one amino acid deletion compared to native SDF-1

A further application of CXCR4 antagonists may also be in the field of cancer therapy. Since the growth of solid tumors is angiogenesis-dependent, and the endothelial cells (essential for the blood vessels formation) carry the SDF-1 receptor, it is possible that SDF-1-derived antagonists may inhibit tumor growth by their anti-angiogenesis effect.

General methods for gene therapy are known in the art. See for example, U.S. Pat. No. 5,399,346 by Anderson et al. A bicompatible capsule for delivery genetic material is described in PCT Publication WO 95/05452 by Baetge et al. Methods for grafting genetically modified cells to treat central nervous system disorders are described in U.S. Pat. No. 5,082,670 and in PCT Publications WO 90/06757 and WO 93/10234, all by Gage et al.

Furthermore, alternative to expression of an SDF-1 derived peptide to inhibit gamma interferon production or inhibit angiogenesis, an antisense oligonucleotide that is complementary to a region of the SDF-1 precursor protein mRNA corresponding to the peptides described herein can be expressed in a subject to inhibit gamma interferon production or inhibit angiogenesis. General methods for expressing antisense oligonucleotides to modulate nervous system disorders are described in PCT Publication WO 95/09236.

Peptides may be prepared in accordance with standard methods (such as disclosed in Clark-Lewis, I., Dewald, B., Loetscher, M., Moser, B., and Baggiolini, M., (1994) J. Biol. Chem., 269, 16075–16081) and assayed for CXCR4 antagonists activity in accordance with standard methods. Peptides may be purified by HPLC and analyzed by mass spectrometry. Peptides may be dimerized via a disulfide bridge formed by gentle oxidation of the cysteines using 10% DMSO in water. Following HPLC purification dimer formation may be verified, by mass spectrometry.

For CXCR4 antagonist assays, human peripheral blood mononuclear cells may be isolated using standard methods, such as from donor blood buffy coats by centrifugation on Ficoll-Paque. The cells may be treated with phytohemagglutinin (1.0 $\mu$g.ml$^{-1}$) and expanded in the presence of IL-2 (100U.ml$^{-1}$) for 7 to 17 days as described (Loetscher, P., Seitz, M., Clark-Lewis, I., Baggiolini, M., and Moser, B., (1994) FASEB J., 8, 1055–1060). These cells may be used as the "T-lymphocytes" for various assays of CXCR4 receptor activity. CEM cells, a human lymphoblastoid CD4$^+$T cell line (ATCC, Rockville, Md.), may be cultured in RPMI medium containing 15 $\mu$g.ml$^{-1}$ of 8-azaguanine (Aldrich Chemical Company, Milwaukee, Wis.) and 10% FCS.

Migration of T-lymphocytes or CEM cells may be assessed in accordance with standard methods. Such methods may utilize 48 well chambers (NeuroProbe, Cabin John MD) using collagen-coated polyvinylpyrrolidone-free polycarbonate membranes with 3 $\mu$m pores (Loetscher, P., Seitz, M., Clark-Lewis, I., Baggiolini, M., and Moser, B., (1994) FASEB J., 8, 1055–1060). Migrated cells may be counted in five randomly selected fields at 1000× magnification after migration of 1 h. Disposable Transwell trays (Colstar, Cambridge Mass.) with 6.5 mm diameter chambers and membrane pore size of 3 $\mu$m, may be used to assay chemotaxis of CEM cells. The puutative antagonist, in Hepes-buffered RPMI 1640 supplemented with 10 mg.ml$^{-1}$ BSA (0.6 Ml), may be added to the lower well, and 0.1 ml of CEM cells (1×10$^7$.ml$^{-1}$) in the same medium without agonist was added to the upper wells. The monoclonal antibody 12G5 (von Tscharner, V., Prod'hom, B., Baggiolini, M., and Reuter, H., (1986) Nature, 324, 369–372; R&D Systems, Minneapolis Minn.) may be preincubated with the cells at 10 $\mu$g.ml$^{-1}$ for 15 min at 0° C. The antibody may also be added to the lower well at 10 $\mu$g.ml$^{-1}$. After 2 h, cells that migrated to the lower wells may be counted. Chemotactic migration may be determined by subtraction of cells migrated in medium alone.

The sequences of various peptides assayed for their activity on CXCR4 are shown in FIG. 1. Both the SDF(1–8) and SDF(1–9) peptides induced dose-dependent chemotaxis of CEM cells (FIG. 2a). the concentrations required for 50% of the maximal response (EC50) are summarized in Table 1. The 1–9 peptide was about 1,000-fold less potent than native SDF-1. However the 1–9 was 7-fold more potent than the 1–8 peptide. the peptides were also tested on T-lymphocytes (FIG. 2b) and the results were similar to those obtained with CEM cells, except that the T-lymphocytes were less responsive to SDF-1 or the peptides. The chemoattractant activity of SDF-1(1–9) was fully inhibited by the SDF-1 antagonist, SDF-1(1–67)[P2G] (Crump, M., Gong J. -H., Loetscher, P., Rajarathnam, K., Amara, A., Arenzana-Seisdedos, F., Virelizier, J. -L., Baggiolini, M., Sykes, B. D., and Clark-Lewis, I., (1997) EMBO J., 16, 6996–7007), but not by an IL-8 antagonist which blocks CXCR1 (Crump, M., Gong J. -H., Loetscher, P., Rajarathnam, K., Amara, A., Arenzana-Seisdedos, F., Virelizier, J. -L., Baggiolini, M., Sykes, B. D., and Clark-Lewis, I., (1997) EMBO J., 16, 6996–7007) (FIG. 3).

To investigate the effect of increasing the peptide length to include both the N-terminal CXC motif and RFFESH (SEQ ID NO:5) binding domains, we prepared SDF-1 (1–17). This peptide was more potent than 1–9 but was several fold lower in chemotactic activity than 1–9 dimer (FIG. 2a). Dimerization of 1–17 did not affect its potency (not shown). This suggests that a SDF-1(1–17) peptide in which there is a P2G substitution would be an active CXCR4 antagonist.

Competition for binding of $^{125}$I-labelled SDF-1 to CEM cells may be carried out as described (Crump, M., Gong J.

-H., Loetscher, P., Rajarathnam, K., Amara, A., Arenzana-Seisdedos, F., Virelizier, J. -L., Baggiolini, M., Sykes, B. D., and Clark-Lewis, I., (1997) EMBO J., 16, 6996–7007). MCP-1 and RANTES binding may be measured to THP-1 cells (Gong, J. -H., Uguccioni, M., Dewald, B., Baggiolini, M., and Clark-Lewis, I., (1996) J. Biol. Chem., 271, 10521–10527).

CEM cells may be used to determine the binding of the SDF-1 peptide to CXCR4 (Crump, M., Gong J. -H., Loetscher, P., Rajarathnam, K., Amara, A., Arenzana-Seisdedos, F., Virelizier, J. -L., Baggiolini, M., Sykes, B. D., and Clark-Lewis, I., (1997) EMBO J., 16, 6996–7007). For example, the competition for binding of $^{125}$I-labelled native SDF-1 by unlabelled native SDF-1 and the N-terminal peptides is shown in FIG. 4. The $K_d$ values are summarized in Table 1. To determine whether peptides bind to other chemokine receptors, competition for MCP-1 or RANTES binding to THP-1 cells may be measured. THP-1 cells express CXCR4 as well as a number of CC chemokine receptors, including receptors for MCP-1 and RANTES.

T-lymphocytes and CEM cells loaded with Fura-2 may be stimulated with the putative antagonist, and the $[Ca^{2+}]_i$-related fluorescence changes recorded from 0–60 s (Jones, S. A., Dewald, B., Clark-Lewis, I., and Baggiolini, M., (1997) J. Biol. Chem., 272, 16166–16169). Receptor desensitization may be tested by monitoring changes during sequential additions at 60 s intervals. Cells may be preincubated with the 12G5 antibody prior to chemokine treatment.

Figure 6:
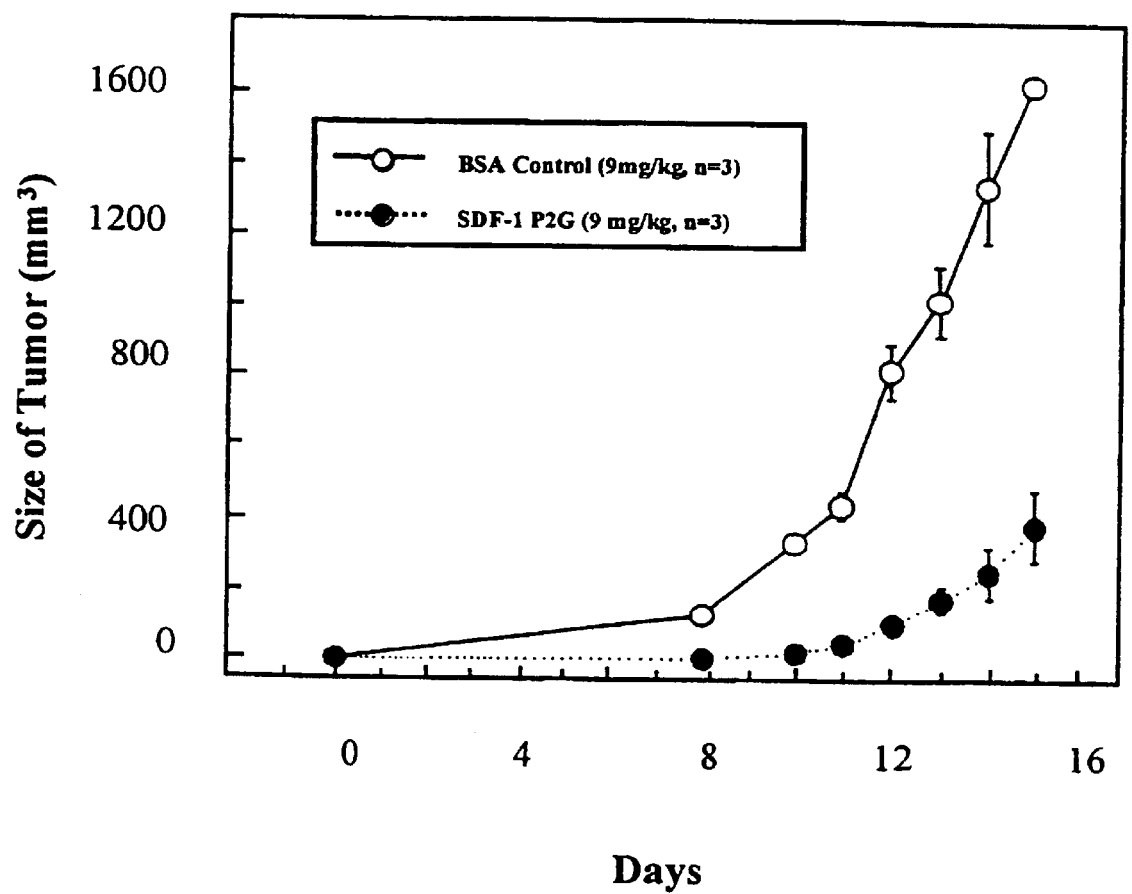
FIG. 6: Line-1 lung carcinoma (5×10$^5$/50 μl in PBS buffer) was injected subcutaneously on the back of each BALB/c mouse (male, 6–8 weeks old, purchased from Jackson Labs, Bar Harbour, Me.). The mice were blindly divided into four groups (three of each group). Immediately after the implantation, the mice received ip. or sc. injection of SDF-1P2G (9 mg/kg in 100 μl PBS buffer). Control mice were injected with the same dose of bovine serum albumin (BSA) or PBS buffer only. The injection was once daily. The size of the tumor was recorded on a daily basis. On day 16, the mass of tumor was determined. The sections of tumor and lung were stained and morphologically observed for blood vessels and metastasis. Shown is the mean value ± SEM of the tumor size.

CXCR4 agonists, such as native SDF-1 and the N-terminal peptides, induce a rapid and transient rise in cytoplasmic concentration, $[Ca^{2+}]_i$, in T-lymphocytes (FIG. 5a) as well as CEM cells (FIG. 6). The rate and magnitude may increase with the concentration. Whereas a response to SDF-1 was observed at $1 \times 10^{-9}$ M, the peptides induced $[Ca^{2+}]_i$ changes in the micromolar range. Receptor usage by SDF-1 derived peptides may be assessed by monitoring $[Ca^{2+}]_i$ changes after sequential stimulation. As shown in FIG. 5a, treatment of T-lymphocytes with SDF-1 completely abolished the responsiveness to the 1–9 peptide, and conversely, the 1–9 peptide also markedly attenuated the response to native SDF-1. The 1–9 dimer (50 µM) completely desensitized the response to subsequent native SDF-1 (not shown). No effect on the response to the 1–9 peptide was observed when T-lymphocytes were pre-stimulated with MCP-1, RANTES, MIP-1β, IP10, or Mig (FIG. 5b). No response to eotaxin, 1–309 or TARC (FIG. 5b) was obtained with these cells under the conditions used, and as expected, they did not desensitize 1–9.

Peptides may be assayed for receptor binding using a CXCR4 blocking monoclonal antibody (von Tscharner, V., Prod'hom, B., Baggiolini, M., and Reuter, H., (1986) Nature, 324, 369–372).

EXAMPLE 1

This example shows the inhibitory effects of CXCR4 antagonists on tumor growth using mouse models.

Tow CXCR4 antagonists used were: (i) the full length SDF-1 antagonist, SDF-1(1–67)[P2G]; and (ii) the short peptide dimer antagonist, SDF-1(1–9[P2G])$_2$. Two animal models used were: (i) the Lewis lung carcinoma on its syngeneic host, the C57BL/6 mice; and (ii) the line-1 carcinoma (a weakly antigenic, highly malignant metastasis model) on its syngeneic host, the BALB/c mice. Male mice, 1.5–3 months old were used.

Treatment protocols were as follows. On day 0, tumor cells ($1-2 \times 10^6$) were subcutaneously (SC) implanted on the back of each mouse. Treatment with the CXCR4 antagonists started immediately after the tumor implantation. The SDF-1(1–67)[P2G] (9 mg/kg/day) or the SDF(1–9[P2G])$_2$ dimer (18 mg/kg/day), dissolved in phosphate buffer, were intraperitoneally (ip), as indicated in the Figures. The injection was once a day for a total of 12–16 days. Tumor size was determined with micrometer and the volume of the tumor was calculated by the form of width$^2 \times$length. Tumor mass was determined at the end of each experiment.

Figure 7:
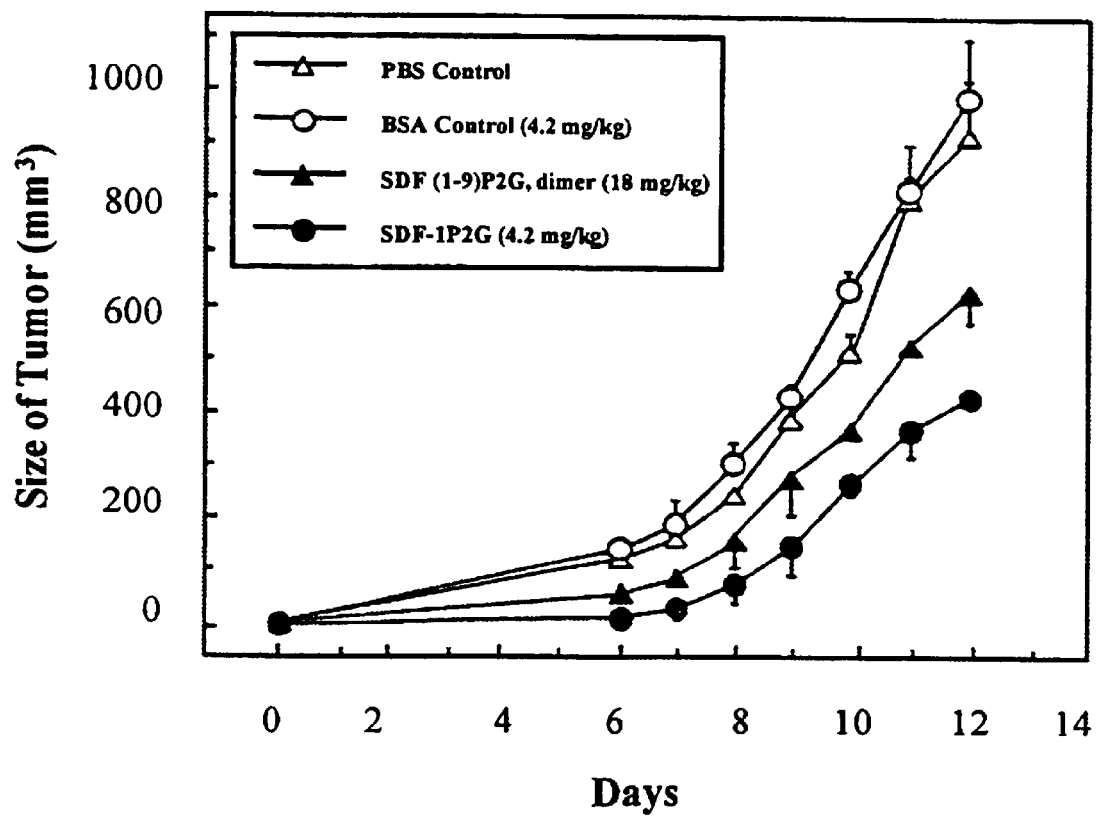
FIG. 7: Line-1 carcinoma cells (1×10$^6$/mouse) were implanted (sc.) as described above. The mice were blindly divided into 4 groups (2 of each), and treated with SDF-1P2G (9 mg/kg), or the dimer form of SDF (1–9) P2G (18 mg/kg). the control groups were injected with PBS buffer alone or BSA. The injection was ip., daily. The size and mass of tumors were determined as above. On day 1 2 the histology of the tumor was studied. Shown is the mean ± SEM of the tumor size.
Figure 9:
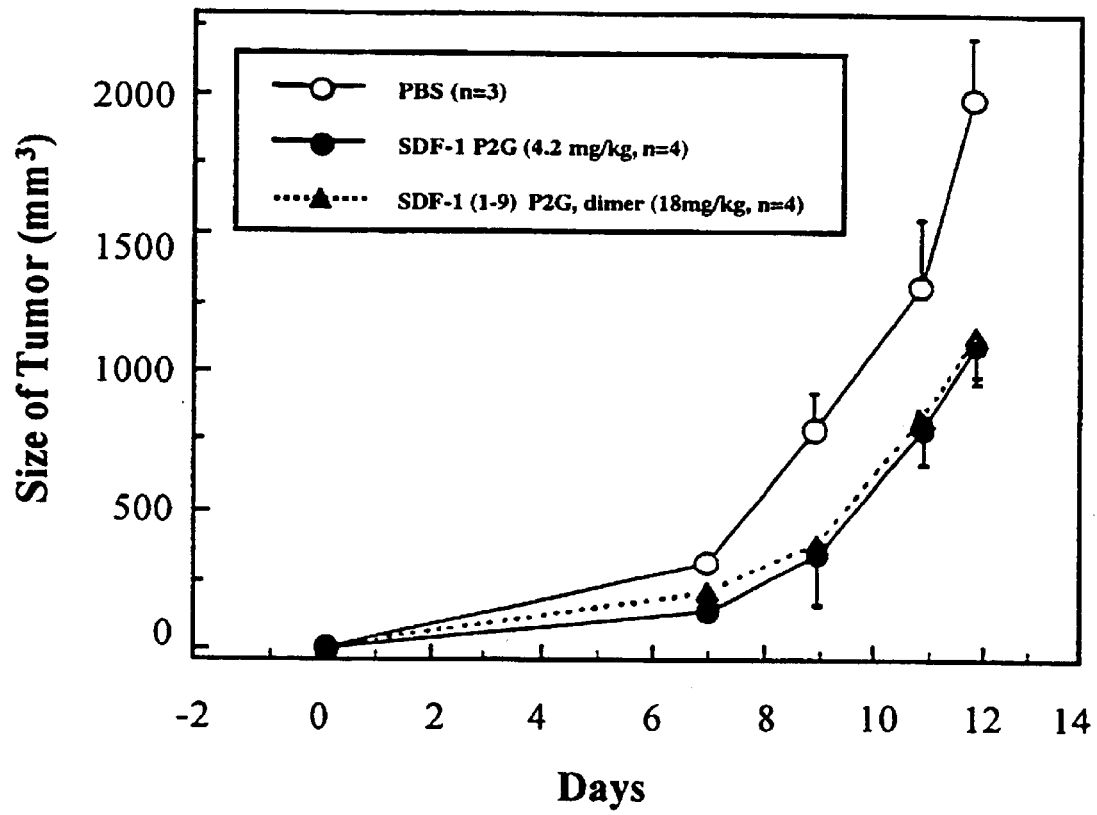
FIG. 9: Inhibition of mouse lung carcinoma (Lewis lung carcinoma) growth by full length SDF-1 antagonist or by short peptide antagonist.

Both the full length (SDF-1 P2G) and the short peptide SDF-1 derived CXCR4 antagonists inhibited the line-1 and Lewis lung carcinoma growth. When compared to the day 12 controls, the SDF-1(1–67)[P2G] inhibited the line-1 lung carcinoma growth by >80%, at a dose of 9 mg/kg (FIG. 6) or 64%, at a dose of 4 mg/kg (FIG. 7). For Lewis lung carcinoma, at day 12, the SDF-1(1–67)[P2G] inhibited the tumor growth by 45%, at a dose of 4 mg/kg (FIG. 9). Subcutaneous injection also inhibited tumor growth, however, the efficiency was less than that of ip. Injection.

Figure 8:
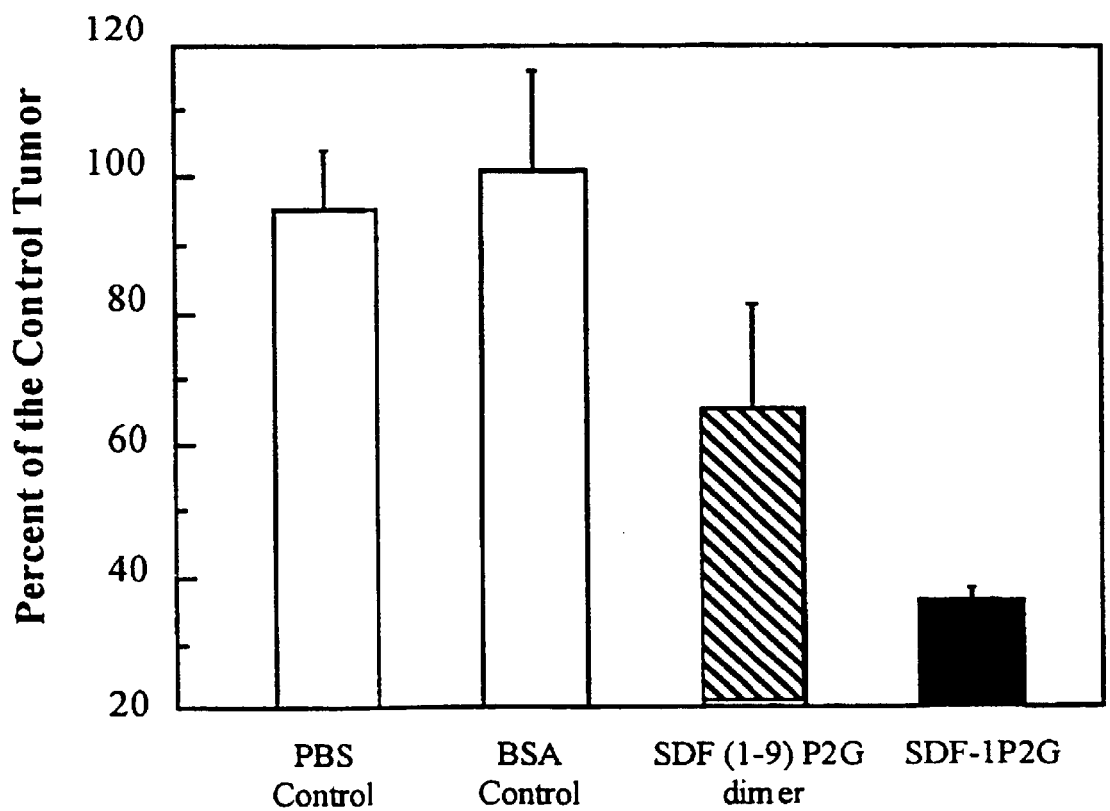
FIG. 8: The mass of the tumor from the experiment in FIG. 7.
Figure 10:
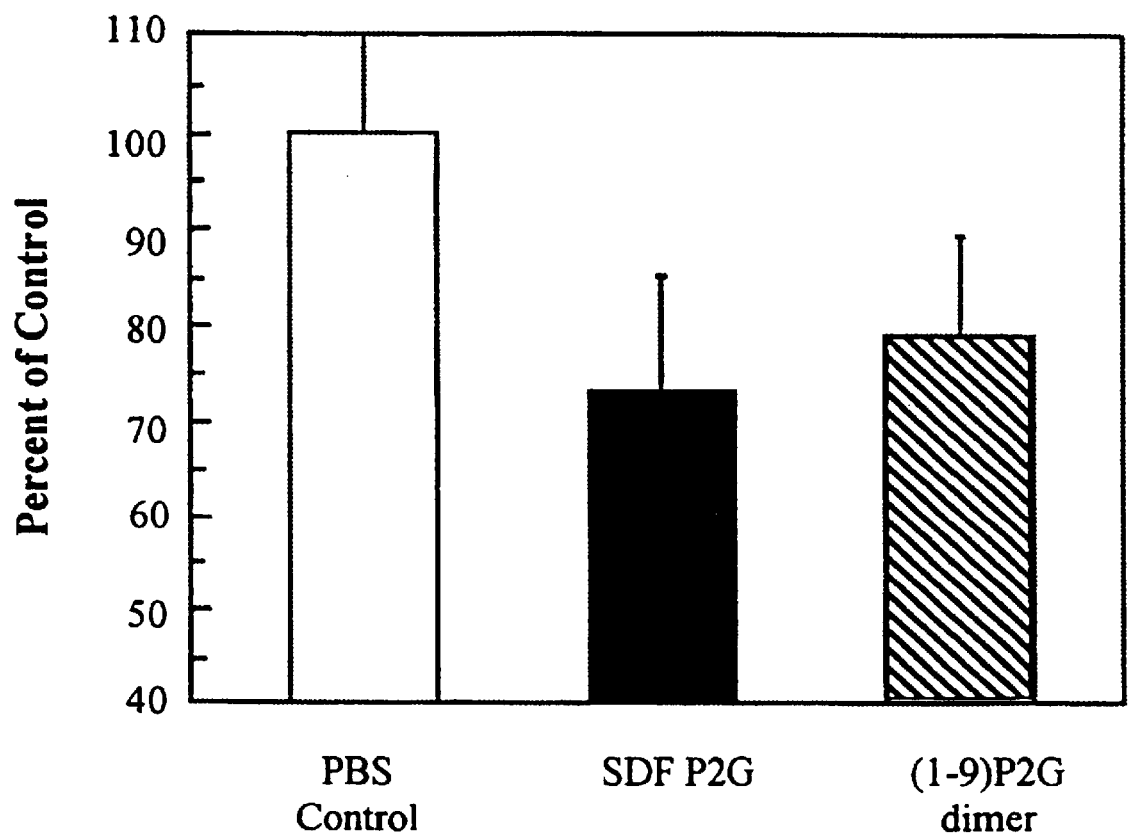
FIG. 10: Mass of tumor (Lewis lung carcinoma) on day 12.
Figure 11:
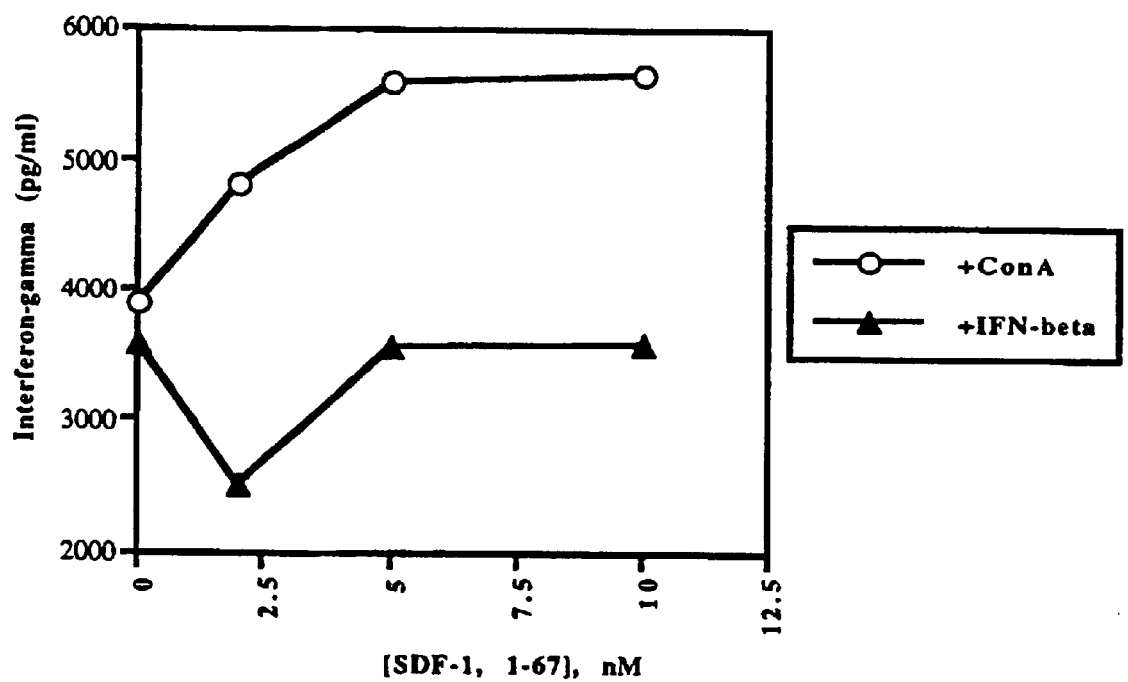
FIG. 11: Effect of SDF-1 on ConA-stimulated Interferon-gamma production in human T-cells.
Figure 12:
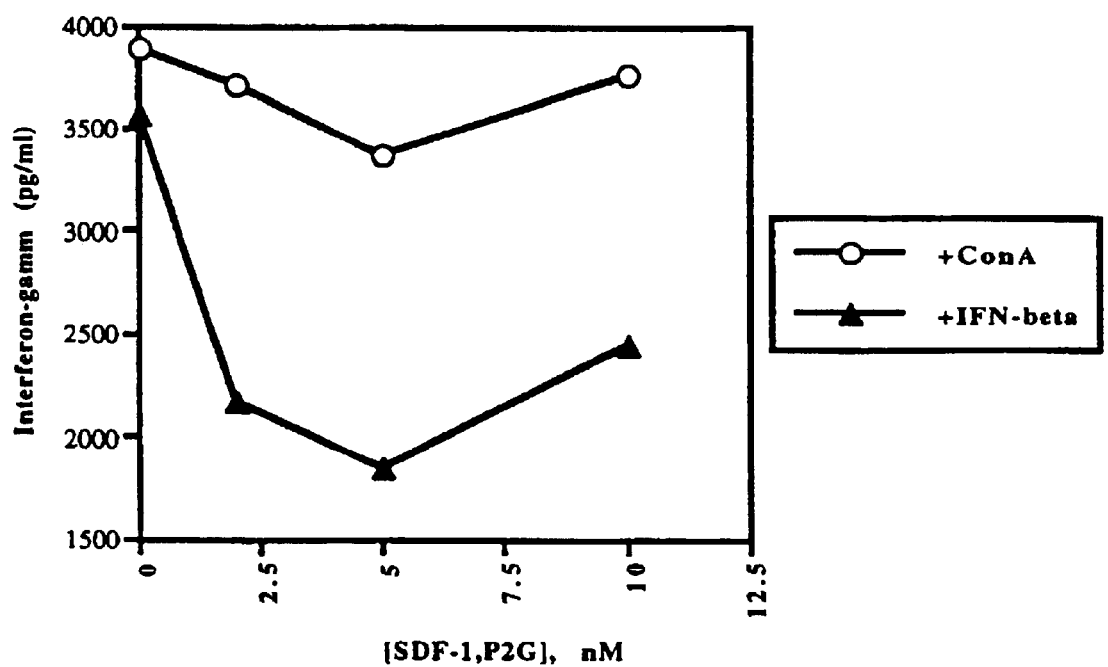
FIG. 12: Effect on SDF-1 antagonist on ConA-stimulated interferon-gamma production in human T-cells.
Figure 13:
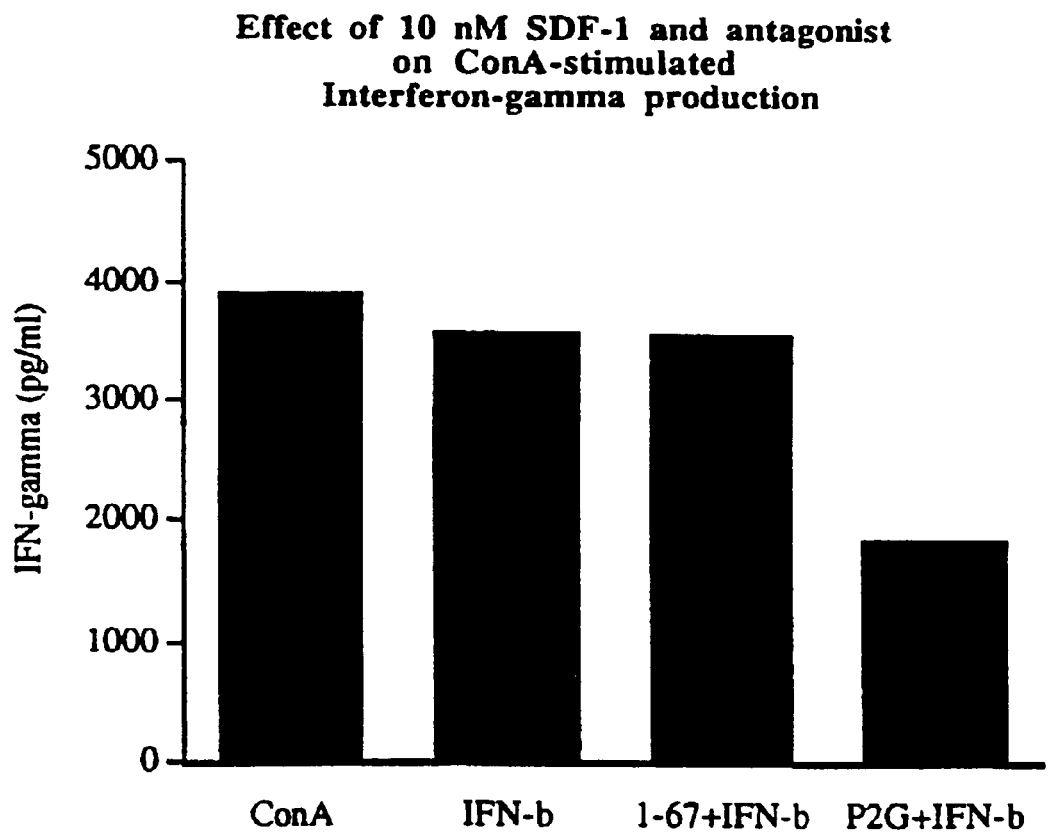
FIG. 13: Effect on 10 nM SDF-1 and antagonist on 10 nM ConA-stimulated Interferon-gamma production.

The degree of tumor growth inhibition by CXCR4 inhibitors correlated with the compounds degree of CXCR4 antagonist activity. The SDF(1–9)P2G dimer was generally a less potent inhibitor of tumor growth than the full length SDF-1(1–67)[P2G] analogue. This indicates that it is the antagonistic activity of these compounds that mediates their chemotherapeutic effect. Nevertheless, even the SDF(1–9) P2G dimer exhibited significant tumor growth inhibiting activity. At a dose of 18 mg/kg The SDF(1–9)P2G dimer inhibited the growth of the Line-1 tumor by 35% at day 12, and inhibited the growth of the Lewis lung carcinoma by 43% at day 12. Tumor mass generally correlated to that of the tumor size determination (FIGS. 8 & 10).

Histological studies show that the tumors from the CXCR4 antagonist treated mice had a lower density of blood vessels than tumors in the control mice, indicating that SDF-1 antagonists act as an angiogenesis inhibitors to reduce neovascularization of tumors.

In the mouse models, no toxicity of CXCR4 antagonists was detected during treatment up to the dose of 18 mg/kg.

EXAMPLE 2

This example shows the inhibition by CXCR4 inhibitors of interferon-gamma production by activated T-cells.

T-cells were isolated and cultured using standard methods as follows. Human blood was taken by venipuncture from healthy donors. Blood was drawn into an anti-coagulatant solution (ACD), mixed with and equal volume of saline solution and layered over Histopaque. Following centrifugation (1200 rpm, 30 minutes), the upper plasma solution was discarded and cells at the interface between the solutions were collected. Cells were washed twice by resuspending in Tyrode's buffer and centrifugation to pellet the cells. The final cell pellet was resuspended in RPMI 1640 containing antibiotics and 20% fetal bovine serum. Cells were plated into tissue culture flasks for 2 hours to allow adherent cells to attach. The non-adherent cells (enriched with T-lymphocytes) were counted using Trypan blue to detect viable cells. Cells were cultured at an initial concentration of 1×106 per ml for 48 hours at 37° C. in a humidified incubator with 5% CO$_2$, 95% air. Additions of Concanavalin A at 1 µg/ml, 1000 Units/ml of interferon-beta, and/or peptides at various concentrations were made at the 0 time point. To assay for interferon-gamma production, the cell suspension was centrifuged to pellet cells and the supernatant was assayed using a commercial ELISA assay kit (Pharmingen).

Table 2 shows interferon-gamma produced by T-cells in culture following stimulation with 1 µg/ml Concanavalin A (Con. A) in the presence of various concentrations of SDF-1 (i.e., 0, 2.5, 5, 7.5 or 10 nM). In these studies, cells treated with interferon beta did not generate more interferon gamma in response to SDF-1. However, significant decrease in the production of interferon gamma was seen when the cells were stimulated with interferon beta synergistically with SDF-1(1–67)[P2G].

TABLE 1

Gamma Interferon Production (pg/ml gamma interferon)

| | SDF-1 Concentration (nM) | | | | |
|---|---|---|---|---|---|
| | 0 | 2.5 | 5 | 7.5 | 10 |
| Control (Con. A) | 3,900 | 4,850 | 5,700 | 5,750 | 5,760 |
| Beta Interferon treated | 3,800 | 2,600 | 3,700 | 3,700 | 3,800 |

Table 1 demonstrates that the level of interferon gamma released from T-cells in cultures in response to stimulation with Concanavalin A is almost 4,000 pg/ml, and this is reduced by treatment with interferon beta. Treatment of T-cells with SDF-1 at the same time as Concanavalin A enhances the production of interferon gamma. There is no effect of SDF-1 addition in reversing the effect of interferon beta.

In contrast, SDF-1 derived CXCR4 antagonists have a significant effect on the production of gamma interferon from the T-cells. This is demonstrated by experiments similar to the studies with interferon beta. Human lymphocytes were exposed to various concentrations of SDF-1 antagonist (SDF-1-P2G and then the cells were activated with Concanavalin A (Con. A). Production of interferon gamma from T-cells exposed to SDF-1 antagonist was measured and compared to the amount released from T-cells that were not treated with the antagonist.

Table 2 demonstrates the effect of a CXCR4 antagonist (SDF-1(1–67)[P2G]) on the release of gamma interferon from T-cells activated by Concanavalin A (Con. A), in the presence and in the absence (control) of beta interferon treatment.

TABLE 2

| | SDF-1(1-67)[P2G] Concentration (nM) | | | |
|---|---|---|---|---|
| | 0 | 2.5 | 5 | 10 |
| Control | 3,900 | 3,700 | 3,400 | 3,600 |
| Beta Interferon Treatment | 3,500 | 2,100 | 1,800 | 2,400 |

The data in Table 2 demonstrates that a CXCR4 antagonist can diminish the release of interferon gamma by the T-cells. Furthermore, when the SDF-1 antagonist is added together with the interferon beta, there is an even greater effect on the reduction on interferon gamma production. Accordingly, a CXCR4 antagonist may be used together with interferon beta to reduce gamma interferon production by activated T-cells, for example T-cells that have been physiologically activated in a patient. For example, CXCR4 antagonists may be used with interferon beta in the treatment of patients with MS.

Table 3 shows the different effects of a CXCR4 agonist (SDF-1) and a CXCR4 antagonist (SDF-1(1–67)[P2G]), when each is used with interferon beta, on the production of interferon gamma from the Con. A activated T-cells. For comparison, Table 4 also shows data for interferon beta alone.

TABLE 3

Effect of 10 nM SDF-1 and SDF-1(1-67)[P2G] (Antagonist) on the Production of Interferon Gamma from Human T-cells

| | Interferon gamma (pg/ml) |
|---|---|
| Control (Con. A) | 3,950 |
| Interferon beta | 3,500 |
| SDF-1 + Interferon beta | 3,500 |
| Antagonist (SDF-1-P2G) + Interferon beta | 1,300 |

The CXCR4 antagonist (SDF-1(1–67)[P2G]) is able to synergistically potentiate the effect of interferon beta in down regulating the production of interferon gamma from activated T-cells. Addition of interferon beta by itself had a small effect on the reduction of interferon gamma release from T-cells. The SDF-1 treatment does not change the effect of interferon beta, but the SDF-1 antagonist (SDF-1-P2G) causes a dramatic reduction in interferon-gamma production.

Table 4 shows the different effects of a CXCR4 antagonist (SDF-1(1–67)[P2G]) on the release of gamma interferon from T-cells activated by concanavilin A (Con.A) in the absence of beta interferon.

TABLE 4

Effect of 0.1 $\mu$M and 1 $\mu$M SDF-1(1-67)[P2G] on the Production of Interferon Gamma from Human T-cells

| | Interferon gamma (pg/ml) |
|---|---|
| Control (unstimulated) | 80 |
| Con. A (activated) | 2,200 |
| Con. A + SDF-1(1-67)[P2G] (0.1 $\mu$M) | 1,050 |
| Con. A + SDF-1(1-67)[P2G] (1 $\mu$M) | 1,100 |

The data in Table 4 demonstrates that a CXCR4 antagonist can diminish the release of interferon gamma by T-cells. Accordingly, a CXCR4 antagonist may be used to reduce interferon gamma production by activated T-cells, for example, T-cells that have been physiologically activated in a patient suffering from multiple sclorosis.

Table 5 shows the different effects of a CXCR4 antagonist (SDF-1(1–9)P2G) on the release of gamma interferon from T-cells activated by concanavalin A (Con.A) in the absence of beta interferon.

TABLE 5

Effect of 1 $\mu$M and 10 $\mu$M SDF-1(1-9)[P2G] on the Production of Interferon Gamma from Human T-cells

| | Interferon gamma (pg/ml) |
|---|---|
| Control (unstimulated) | 100 |
| Con. A (activated) | 2,200 |
| Con. A + SDF-1(1-9)[P2G] (1 $\mu$M) | 1,100 |
| Con. A + SDF-1(1-9)[P2G] (10 $\mu$M) | 1,000 |

The data in Table 5 further demonstrates that a shortened peptide CXCR4 antagonist can diminish the release of interferon gamma by T-cells. Accordingly, a CXCR4 antagonist of a shorter length may be used to reduce interferon gamma production by activated T-cells.

What is claimed is:

1. A therapeutic composition comprising a CXCR4 antagonist and a pharmacologically acceptable excipient wherein the antagonist is a protein that comprises an N-terminal sequence of KGVSLSYR (SEQ ID NO: 3).

2. The therapeutic composition of claim 1 further comprising interferon beta.

3. A polymeric CXCR4 antagonist comprising a plurality of peptides covalently joined by a bridging moiety so that the polymeric CXCR4 antagonist has a plurality of N-terminals having their first eight amino acids comprising KGVSLSYR (SEQ ID NO: 3).

4. The polymeric CXCR4 antagonist according to claim 3, wherein the antagonist is SDF-1(1–9[P2G])$_2$.

5. The antagonist of claim 3 in a pharmacologically acceptable formulation.

6. The antagonist of claim 3 in combination with a pharmaceutically acceptable excipient.

7. A CXCR4 antagonist comprising an N-terminal amino acid sequence of KGVSLSYR (SEQ ID NO: 3).

8. The antagonist of claim 7 in combination with beta interferon.

9. A CXCR4 antagonist according to claim 7, wherein the peptide compound comprises a dimer of SEQ ID NO:3 according to the following formula:

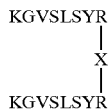

KGVSLSYR
|
X
|
KGVSLSYR wherein X is lysine and both the α- and ε-amino groups of the lysine are associated with amide bond formation and the lysyl carboxyl group is protected.

10. A CXCR4 antagonist according to claim 7, wherein the peptide compound comprises a dimer of SEQ ID NO:4 according to the following formula:

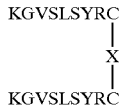

KGVSLSYRC
|
X
|
KGVSLSYRC wherein X is lysine and both the α- and ε-amino groups of the lysine are associated with amide bond formation and the lysyl carboxyl group is protected.

11. A CXCR4 antagonist according to claim 7, wherein the peptide compound consists of a dimer of SEQ ID NO:3 according to the following formula:

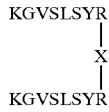

KGVSLSYR
|
X
|
KGVSLSYR wherein X is lysine and both the α- and ε-amino groups of the lysine are associated with amide bond formation and the lysyl carboxyl group is protected.

12. A CXCR4 antagonist according to claim 7, wherein the peptide compound consists of a dimer of SEQ ID NO:4 according to the following formula:

KGVSLSYRC
|
X
|
KGVSLSYRC wherein X is lysine and both the α- and ε-amino groups of the lysine are associated with amide bond formation and the lysyl carboxyl group is protected.

13. A CXCR4 antagonist consisting of KGVSLSYR (SEQ ID NO: 3).

14. A therapeutic composition comprising a CXCR4 antagonist and a pharmacologically acceptable excipient wherein the antagonist consists of KGVSLSYR (SEQ ID NO: 3).

15. The therapeutic composition of claim 14 further comprising interferon beta.

16. A polymeric CXCR4 antagonist comprising a plurality of peptides covalently joined by a bridging moiety so that the polymeric CXCR4 antagonist has a plurality of N-terminals consisting of KGVSLSYC (SEQ ID NO: 4).

17. A CXCR4 antagonist consisting of KGVSLSYRC (SEQ ID NO: 4).

18. A therapeutic composition comprising a CXCR4 antagonist and a pharmacologically acceptable excipient wherein the antagonist consists of KGVSLSYRC (SEQ ID NO: 4).

19. The therapeutic composition of claim 18 further comprising interferon beta.

20. A polymeric CXCR4 antagonist comprising a plurality of peptides covalently joined by a bridging moiety so that the polymeric CXCR4 antagonist has a plurality of N-terminals consisting of KGVSLSYRC (SEQ ID NO: 4).

* * * * *

SEQUENCE LISTING

<160> NUMBER OF SEQ ID NOS: 7

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence:two putative
      CXCR4 binding sites joined by the CXC motif

<400> SEQUENCE: 1

Lys Pro Val Ser Leu Ser Tyr Arg Cys Pro Cys Arg Phe Phe Glu Ser
 1               5                  10                  15

His

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence:CXCR4
antagonist peptide compound N-terminal sequence
<221> NAME/KEY: MOD_RES
<222> LOCATION: (9)
<223> OTHER INFORMATION: Xaa = Cys or Cys modified by a polypeptide
homologous to a portion of SDF-1

<400> SEQUENCE: 2

Lys Gly Val Ser Leu Ser Tyr Arg Xaa
1 5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence:CXCR4
antagonist peptide compound of dimerized
N-terminal amino acid sequence
<221> NAME/KEY: MOD_RES
<222> LOCATION: (9)
<223> OTHER INFORMATION: Xaa = Lys, where the epsilon amino group forms
an amide bond to Arg in the peptide
Arg-Tyr-Ser-Leu-Ser-Val-Gly-Lys, represented from
the carboxyl to amino end

<400> SEQUENCE: 3

Lys Gly Val Ser Leu Ser Tyr Arg Xaa
1 5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence:CXCR4
antagonist peptide compound of dimerized
N-terminal amino acid sequence
<221> NAME/KEY: MOD_RES
<222> LOCATION: (10)
<223> OTHER INFORMATION: Xaa = Lys, where the epsilon amino group forms
an amide bond to Cys in the peptide
Cys-Arg-Ser-Leu-Ser-Val-Gly-Lys, represented from
the carboxyl to amino end

<400> SEQUENCE: 4

Lys Gly Val Ser Leu Ser Tyr Arg Cys Xaa
1 5 10

```
<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:upstream
      N-terminal binding site sequence motif

<400> SEQUENCE: 5

Arg Phe Phe Glu Ser His
 1               5

<210> SEQ ID NO 6
<211> LENGTH: 67
<212> TYPE: PRT
<213> ORGANISM: Homo sapiens
<220> FEATURE:
<223> OTHER INFORMATION: stromal cell derived factor-1alpha (SDF-1alpha)

<400> SEQUENCE: 6

Lys Pro Val Ser Leu Ser Tyr Arg Cys Pro Cys Arg Phe Phe Glu Ser
 1               5                  10                  15

His Val Ala Arg Ala Asn Val Lys His Leu Lys Ile Leu Asn Thr Pro
                20                  25                  30

Asn Cys Ala Leu Gln Ile Val Ala Arg Leu Lys Asn Asn Asn Arg Gln
            35                  40                  45

Val Cys Ile Asp Pro Lys Leu Lys Trp Ile Gln Glu Tyr Leu Glu Lys
        50                  55                  60

Ala Leu Asn
 65

<210> SEQ ID NO 7
<211> LENGTH: 72
<212> TYPE: PRT
<213> ORGANISM: Homo sapiens
<220> FEATURE:
<223> OTHER INFORMATION: stromal cell derived factor-1beta (SDF-1beta)

<400> SEQUENCE: 7

Lys Pro Val Ser Leu Ser Tyr Arg Cys Pro Cys Arg Phe Phe Glu Ser
 1               5                  10                  15

His Val Ala Arg Ala Asn Val Lys His Leu Lys Ile Leu Asn Thr Pro
                20                  25                  30

Asn Cys Ala Leu Gln Ile Val Ala Arg Leu Lys Asn Asn Asn Arg Gln
            35                  40                  45

Val Cys Ile Asp Pro Lys Leu Lys Trp Ile Gln Glu Tyr Leu Glu Lys
        50                  55                  60

Ala Leu Asn Lys Arg Phe Lys Met
 65                  70
```